(12) United States Patent
Reback et al.

(10) Patent No.: US 12,285,315 B2
(45) Date of Patent: Apr. 29, 2025

(54) VETERINARY PROCEDURE TABLE SYSTEM

(71) Applicant: Olympic Veterinary Corporation, Mercer Island, WA (US)

(72) Inventors: Joseph D. Reback, Seattle, WA (US); Cole Jason Dalton, Mukilteo, WA (US)

(73) Assignee: OLYMPIC VETERINARY CORPORATION, Tukwila, WA (US)

( * ) Notice: Subject to any disclaimer, the term of this patent is extended or adjusted under 35 U.S.C. 154(b) by 472 days.

(21) Appl. No.: 17/182,688

(22) Filed: Feb. 23, 2021

(65) Prior Publication Data
US 2022/0265411 A1 Aug. 25, 2022

(51) Int. Cl.
*A61D 3/00* (2006.01)
*A61G 13/04* (2006.01)
*A61G 13/08* (2006.01)

(52) U.S. Cl.
CPC ............ *A61D 3/00* (2013.01); *A61G 13/04* (2013.01); *A61G 13/08* (2013.01)

(58) Field of Classification Search
CPC .......... A61D 3/00; A61G 13/04; A61G 13/08; A61G 13/102
See application file for complete search history.

(56) References Cited

U.S. PATENT DOCUMENTS

| | | | | |
|---|---|---|---|---|
| 3,093,836 A | * | 6/1963 | Christensen | A61G 7/0005 5/606 |
| 4,195,829 A | * | 4/1980 | Reser | A61G 13/02 5/607 |
| 4,558,847 A | * | 12/1985 | Coates | B66F 7/0625 254/9 C |
| 5,224,228 A | * | 7/1993 | Larrimore | A61G 7/001 5/942 |
| 5,303,437 A | * | 4/1994 | Hung | A61G 7/015 5/942 |

(Continued)

OTHER PUBLICATIONS

DRE Veterinary; OP System Veterinary Surgery Table; Available at least as early as Feb. 22, 2021.

(Continued)

*Primary Examiner* — Michael H Wang
(74) *Attorney, Agent, or Firm* — Polsinelli PC

(57) ABSTRACT

A veterinary procedure table system includes a procedure table having an animal support surface assembly supported by a vertical column, wherein the animal support surface assembly is movable between first and second tilted orientations, and wherein the animal support surface assembly is movable between a first animal support surface height position and a second animal support surface height position, and a back table coupled to the vertical column of the procedure table, wherein the back table is movable between a first position relative to the procedure table and a second positon relative to the procedure table, wherein the back table moves with the animal support surface assembly between the first animal support surface height position and the second animal support surface height position, and wherein the back table does not tilt with the animal support surface assembly between the first tilted orientation and the second tilted orientation.

16 Claims, 14 Drawing Sheets

(56) References Cited

U.S. PATENT DOCUMENTS

| | | | |
|---|---|---|---|
| 5,826,286 A * | 10/1998 | Cranston | A61G 13/04 5/942 |
| 6,279,510 B1 | 8/2001 | Batterton | |
| 7,461,825 B2 * | 12/2008 | Olivera | F16M 11/24 248/123.2 |
| 7,472,441 B1 * | 1/2009 | Steffensmeier | A61G 13/04 606/244 |
| 7,716,761 B1 * | 5/2010 | Gilstad | A61G 7/0573 5/607 |
| 8,042,208 B2 * | 10/2011 | Gilbert | A61G 13/04 5/660 |
| 9,355,219 B2 * | 5/2016 | Paydar | G07F 11/62 |
| 9,757,024 B2 * | 9/2017 | Corrigan | A61B 3/0083 |
| 10,881,567 B2 * | 1/2021 | St. John | A61G 7/015 |
| 2007/0125314 A1 | 6/2007 | Keil | |
| 2008/0235876 A1 * | 10/2008 | Sundstrom | A61G 13/04 5/611 |
| 2009/0241262 A1 * | 10/2009 | Jehn | A61G 13/102 5/607 |
| 2009/0255483 A1 * | 10/2009 | Keil | A61D 3/00 119/753 |
| 2015/0040319 A1 * | 2/2015 | Doak | A61G 13/105 5/620 |
| 2015/0327818 A1 * | 11/2015 | Buck | A61G 13/04 5/608 |

OTHER PUBLICATIONS

Midmark Electric Column Surgery Table Manual; Jun. 2, 2020.
Midmark Hydraulic Column Surgery Table Manual; 2017.
Pannomed Trend; Veterinary Surgical Table; Available at least as early as Feb. 22, 2021.
Suburban Surgical Co., Inc.; Operating Table; Available at least as early as Feb. 22, 2021.
Technidyne Corporation; V-Top Dental / Surgery Workstation; available at least as early as Feb. 22, 2021.
Technidyne Corporation; V-Top Surgery Table; available at least as early as Feb. 22, 2021.

* cited by examiner

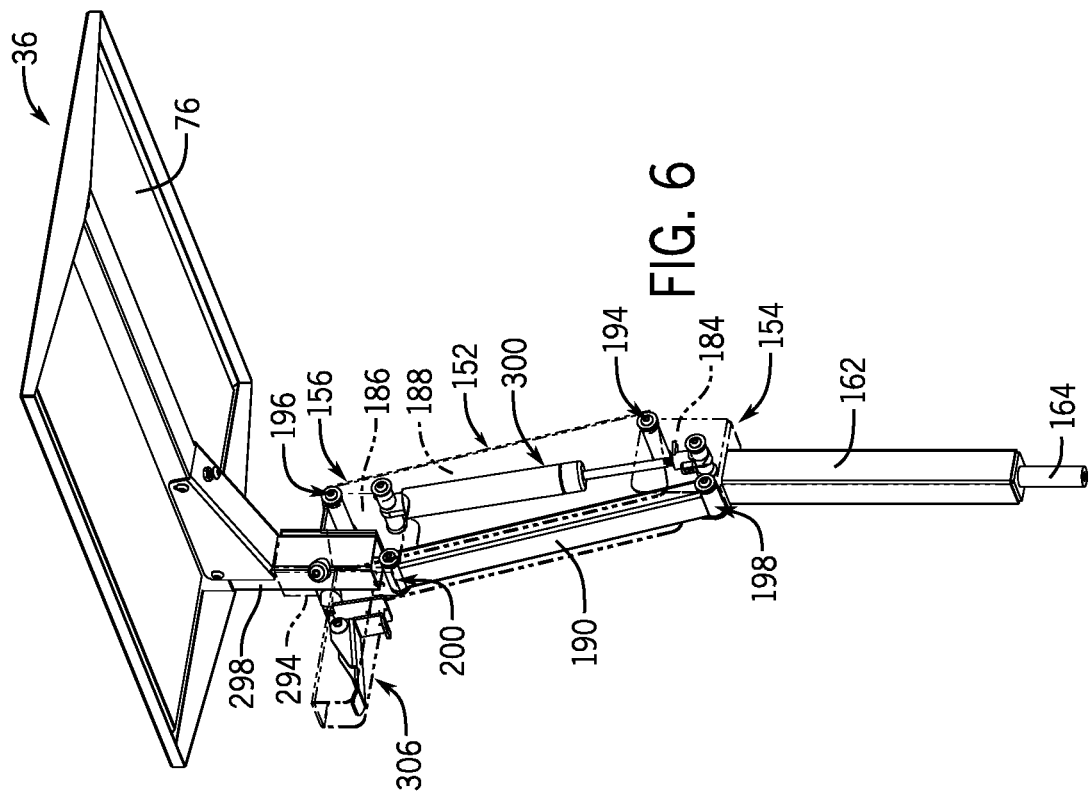
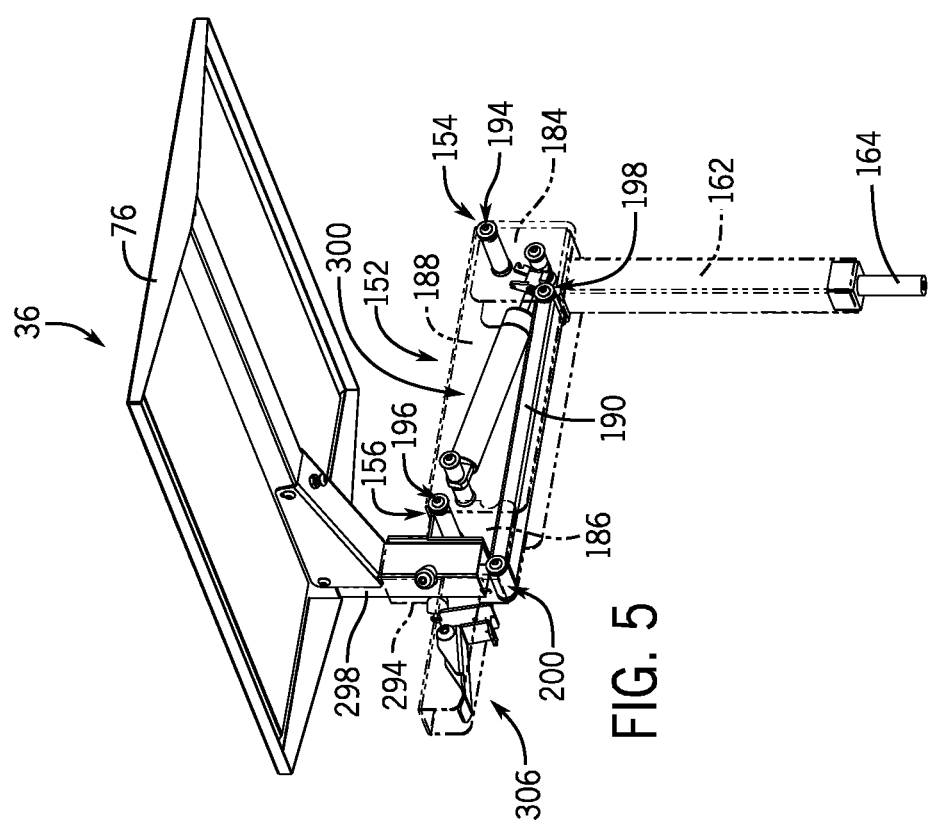

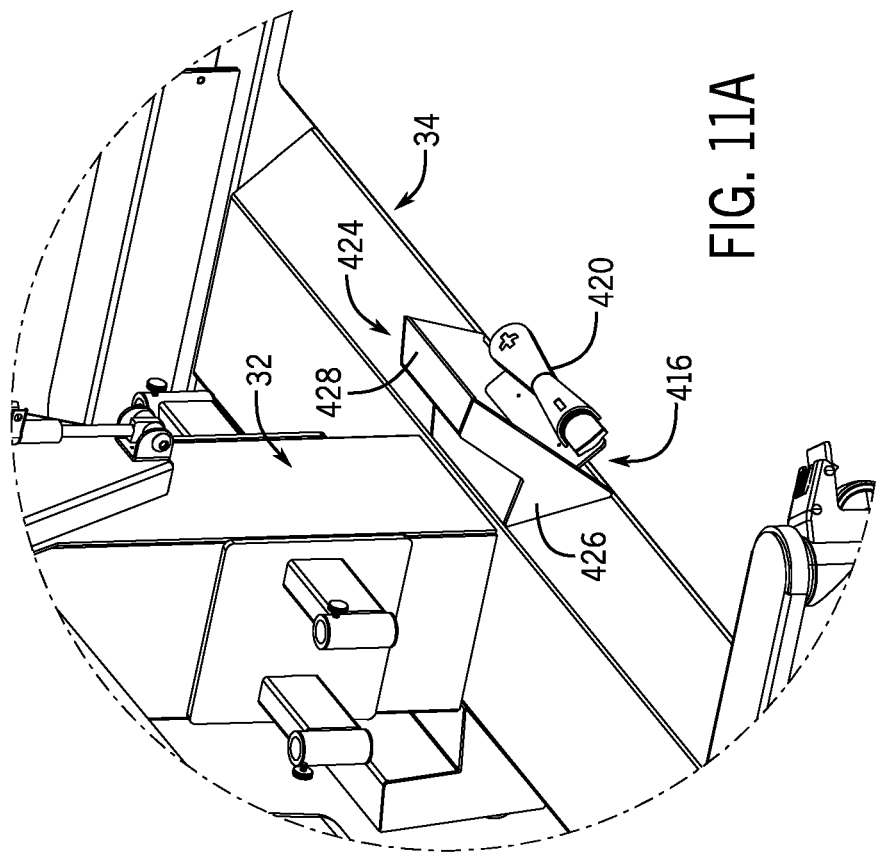
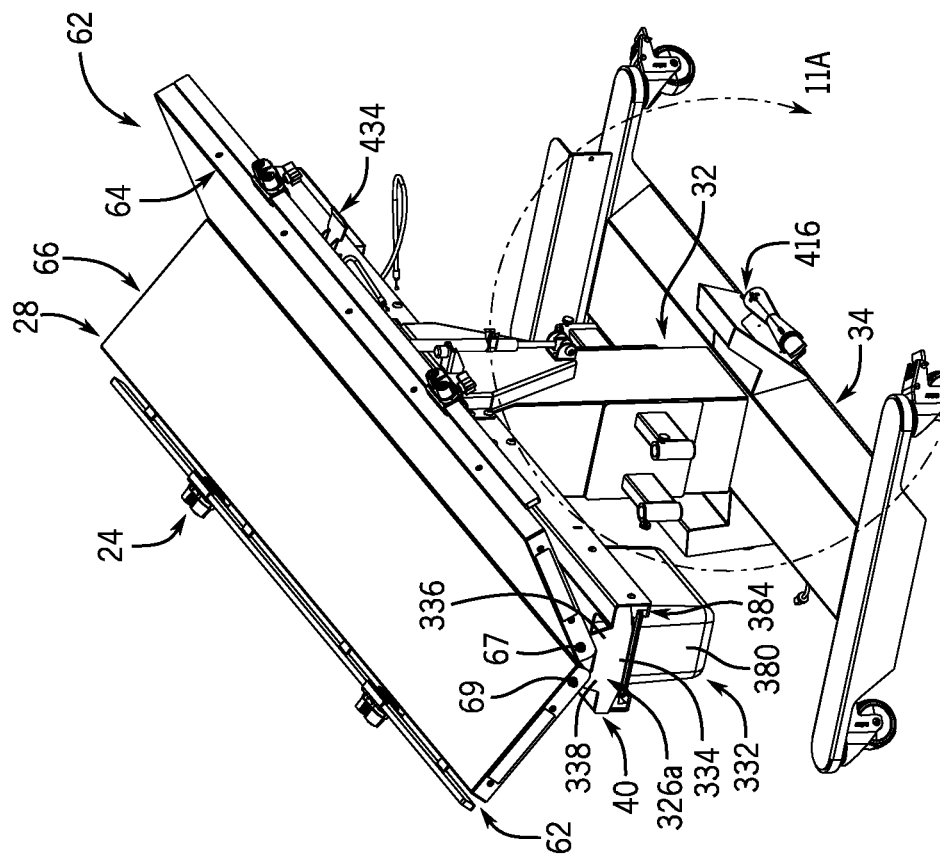

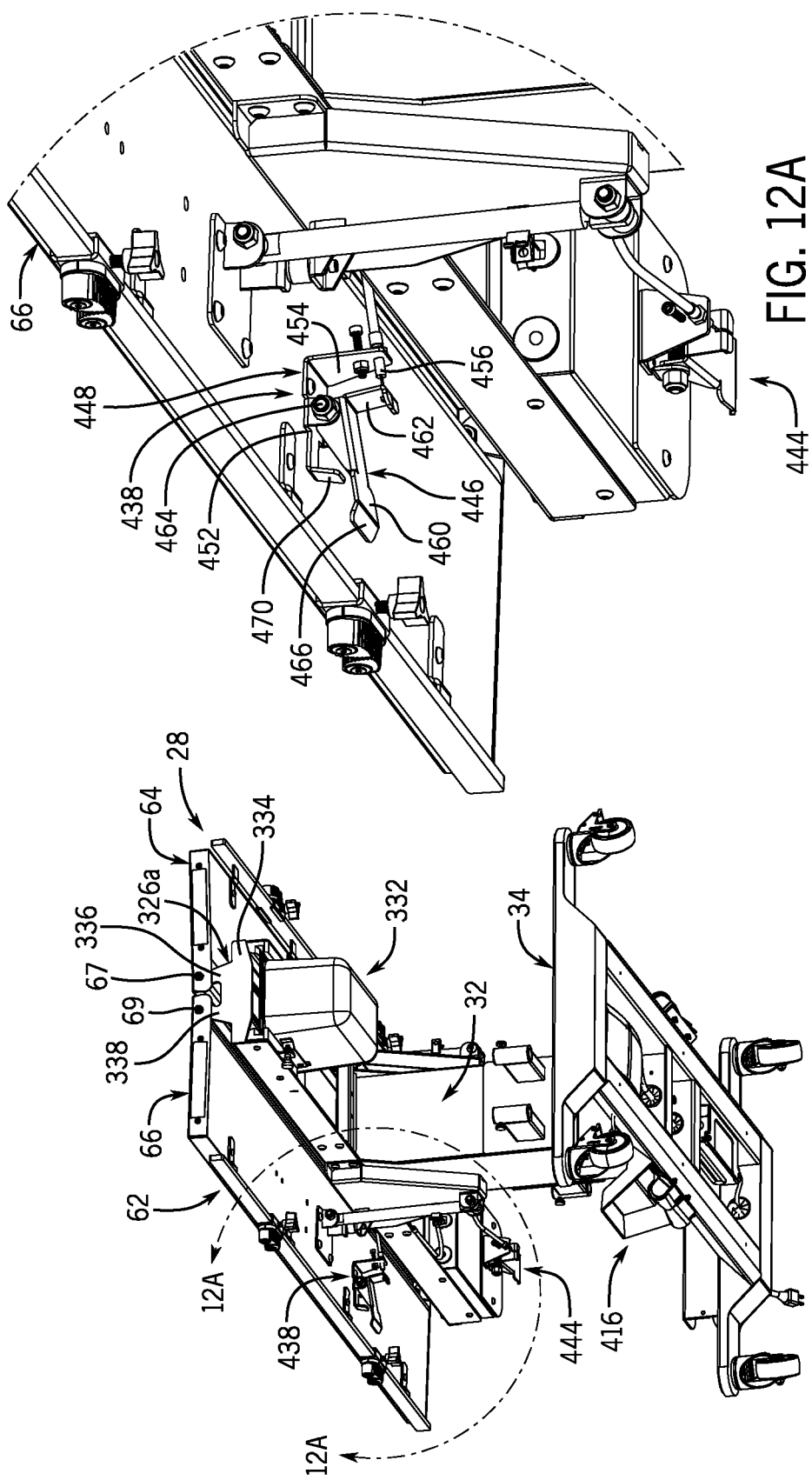

VETERINARY PROCEDURE TABLE SYSTEM

BACKGROUND

A variety of different table systems are used by animal care professionals to provide services for companion animals such as dogs and cats. Veterinary procedure tables (including examination, surgery, treatment, transport, and dental tables) are designed to accommodate many different types of procedures, such as surgery, dental procedures, spay and neutering procedures, limb procedures, eye procedures, etc. Typically, these procedure tables consist of an elevated animal support surface mounted on a vertical column. An animal is positioned on the support surface for the procedure.

Veterinary procedure tables may include an animal support surface that is adjustable in height to better accommodate the various procedures for animals of various sizes. For instance, many veterinary procedure tables allow the height of the animal support surface to be raised or lowered through a lifting mechanism operably connected to the vertical column. With these tables, animal handling issues are minimized because the animal may be placed on the support surface when it is in a lowered position. These tables also provide a variety of animal support surface working heights to accommodate different procedures and practitioners of various heights.

Many veterinary procedure tables also often allow the animal support surface to be tilted or otherwise adjusted in position. For instance, the table may include a hand-adjustable tilt-top mechanism that allows the animal support surface to rotate between various angled positions relative to the vertical column.

A separate back table may be used to hold instruments and other supplies needed during a procedure. Typical prior art back tables are a simple table (i.e., a tabletop and four vertical legs) made from medical grade material. Casters may be mounted to the ends of the table legs such that the back table may be moved around the room as needed. However, such back tables can take up valuable real estate in the procedure room. Moreover, although the height of these tables may be adjusted independently of the procedure table using a manual crank mechanism, they cannot always be optimally positioned next to the procedure table to conveniently retrieve instruments or supplies, especially when the procedure table is in a raised and/or tilted position.

Many veterinary procedure tables also often include an animal support surface defined as a two panel V-top system that adjusts from an elongated flat shape to an elongated V-shape to hold the patient in the desired position during surgery. More specifically, first and second elongated panels are positioned substantially adjacent to one another and pivot along first and second elongated axes between a substantially flat, co-planar position to a raised V-shape position.

During certain procedures, it may be desired to collect fluid materials discharged from the animal ("lavage") or otherwise used during the procedure and to direct these fluids away from the animal support surface to an appropriate drain. For example, the treatment of wounds, the performance of surgery, or various other veterinary procedures may require irrigation or washing of the animal which generates fluids that should be directed away from the animal support surface. Accordingly, veterinary procedure tables may be provided with a basin or channel beneath the two panel V-top system adapted to collect fluids generated during the procedure and to direct these fluids to an appropriate drain or collection unit. However, the fluid may not always flow consistently into the channel, causing the area surrounding the procedure table and/or the components of the table to become unnecessarily soiled. Further, it is difficult to clean the channel beneath the V-top system without removing the channel. Even if the channel can be removed for cleaning, a large area and/or cleaning station would be required.

Accordingly, there is a need for an improved veterinary procedure table system that addresses the foregoing needs and other needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A veterinary procedure table system includes a procedure table having an animal support surface assembly supported by a vertical column, wherein the animal support surface assembly is movable between first and second tilted orientations, and wherein the animal support surface assembly is movable between a first animal support surface height position and a second animal support surface height position. The system further includes a back table coupled to the vertical column of the procedure table, wherein the back table is movable between a first position relative to the procedure table and a second positon relative to the procedure table, wherein the back table moves with the animal support surface assembly between the first animal support surface height position and the second animal support surface height position, and wherein the back table does not tilt with the animal support surface assembly between the first tilted orientation and the second tilted orientation.

A veterinary procedure table system includes a procedure table having an animal support surface assembly supported by a vertical column. The animal support surface assembly includes a first elongated panel, a second elongated panel, and a gap extending between the first and second elongated panels, wherein the first and second elongated panels are moveable between at least an elongated substantially flat, co-planar position and a V-shape position. The system further includes a fluid collection and cleaning assembly configured to collect fluid flowing from the first and second elongated panels in an elongated channel located beneath the first and second elongated panels and further configured to enable cleaning of the elongated channel without having to remove the elongated channel from its location beneath the first and second elongated panels.

A veterinary procedure table system includes a procedure table having an animal support surface assembly supported by a vertical column extending from a base and a foot switch assembly having a foot switch secured to the base and a foot switch roof configured to at least partially cover the foot switch.

A veterinary procedure table system includes a procedure table having an animal support surface assembly supported by a vertical column and at least one release lever assembly configured to operate aspects of the procedure table. The at least one release lever assembly may include a mounting bracket secured beneath the animal support surface assembly, and an L-shaped lever pivotally coupled to a mounting bracket. The L-shaped lever includes a paddle portion configured to be graspable by a user and a cable-pulling portion extending substantially transversely from the paddle portion that connects to a cable.

A veterinary procedure table system includes a procedure table having an animal support surface assembly supported by a vertical column and a rail extending along a length of the animal support surface assembly and an arm rest assembly attachable to the rail that is adjustable in orientation in an unlocked configuration and fixed in orientation in a locked configuration.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows an isometric view of the back table of the veterinary procedure table system of FIG. 1, wherein the back table is in a first height position.

FIG. 6 shows an isometric view of the back table of FIG. 5, wherein the back table is in a second height position.

FIG. 9A shows a cross-sectional view of a channel of the animal support surface assembly of FIG. 9.

FIG. 11 shows an isometric view of the veterinary procedure table system of FIG. 1 having the back table removed.

FIG. 11A shows an isometric zoomed-in view of a foot switch assembly of the veterinary procedure table system of FIG. 11.

FIG. 12 shows an isometric view of the veterinary procedure table system of FIG. 1 having the back table removed.

FIG. 12A shows an isometric zoomed-in view of a lever assembly of the veterinary procedure table system of FIG. 11.

DETAILED DESCRIPTION

Figure 1:
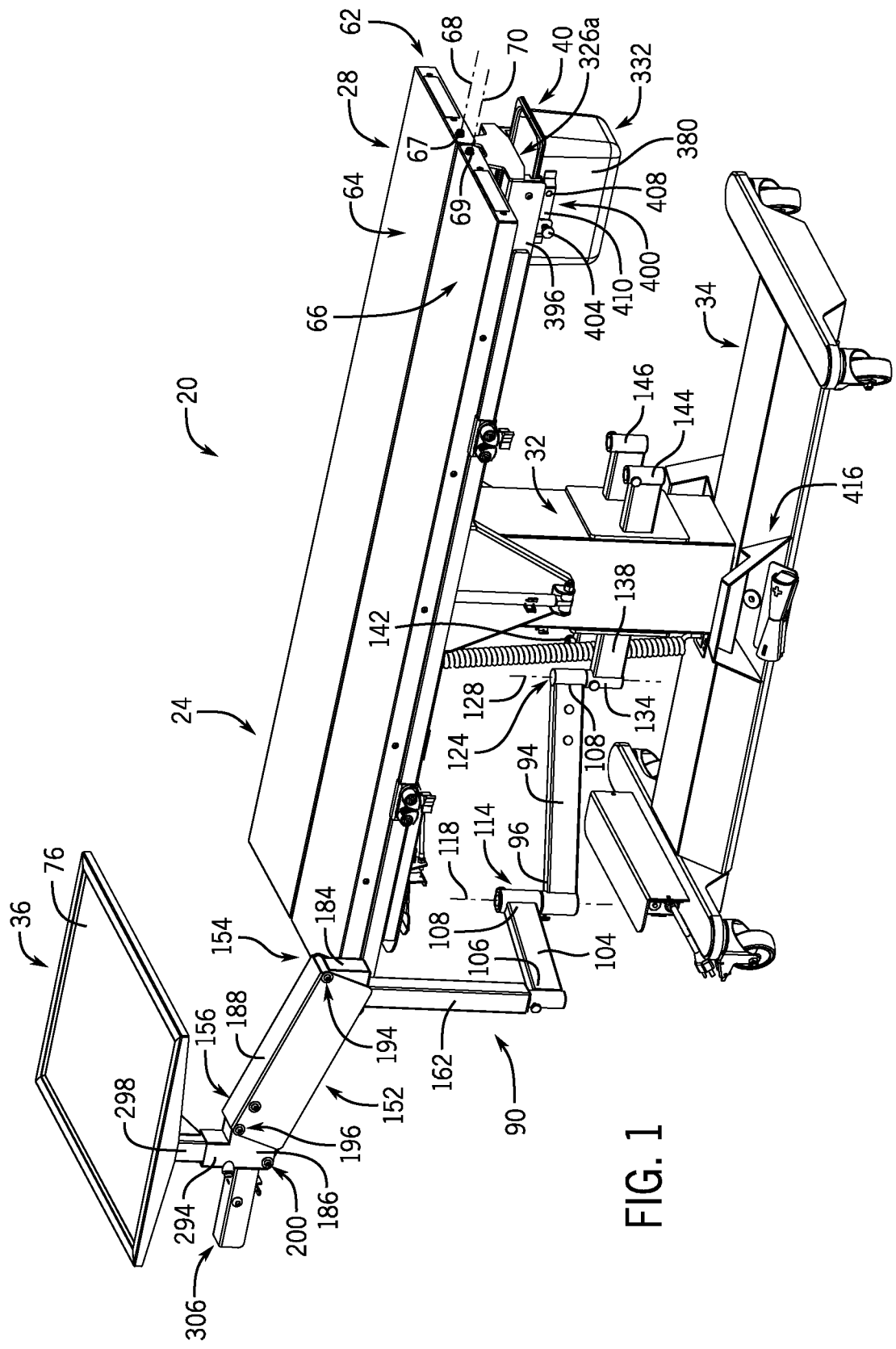
FIG. 1 shows an isometric view of an exemplary embodiment of a veterinary procedure table system having a procedure table and a back table, wherein the back table is in a first circumferential position relative to the procedure table, wherein an animal support surface assembly of the procedure table is in a first height position relative to a base, and wherein the animal support surface assembly of the procedure table is in a first tilted orientation relative to a vertical column extending between the base and the animal support surface assembly.
Figure 2:
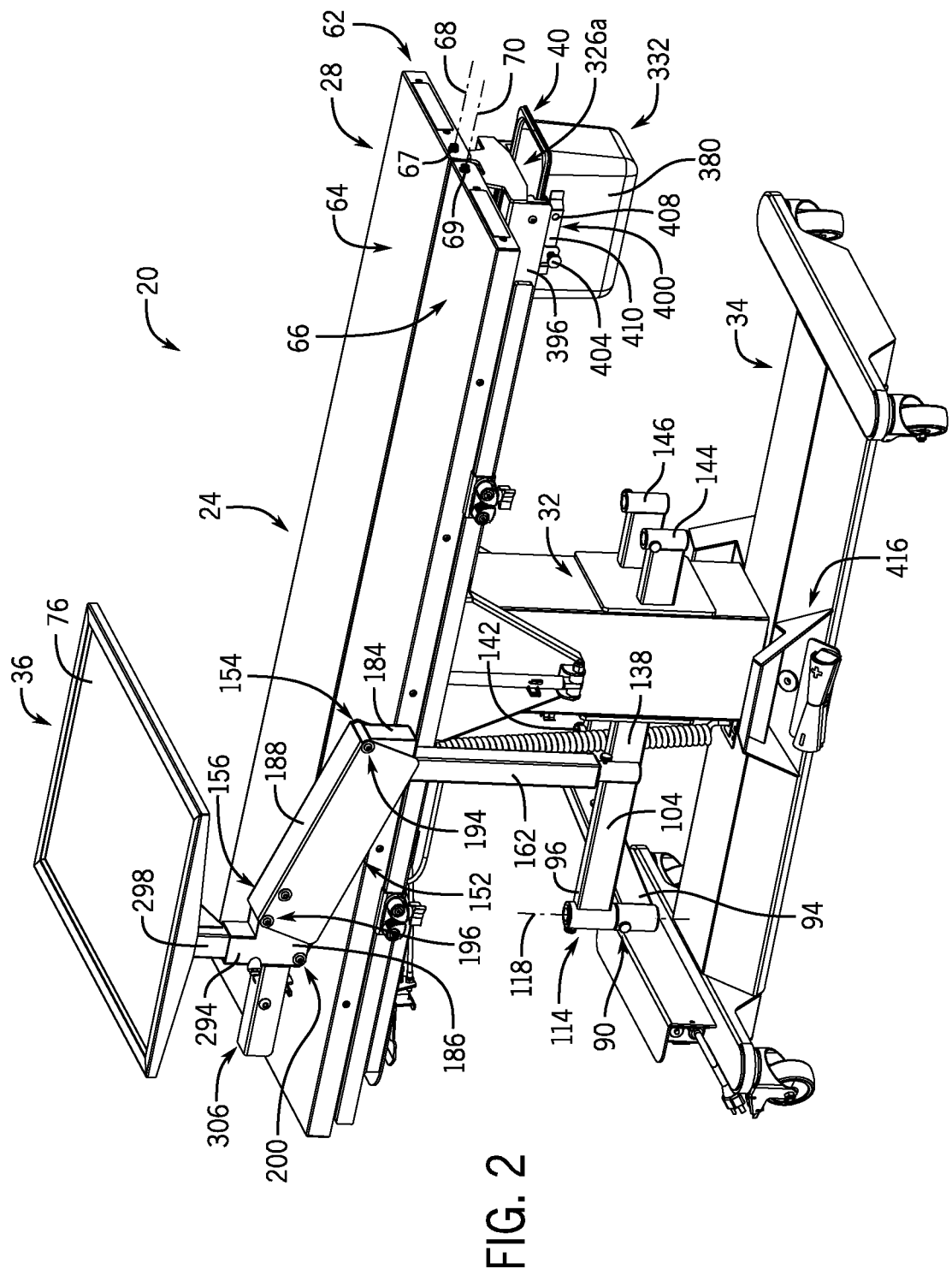
FIG. 2 shows an isometric view of the veterinary procedure table system of FIG. 1, wherein the back table is in a second circumferential position relative to the procedure table, wherein the animal support surface assembly of the procedure table is in the first height position relative to the base, and wherein the animal support surface assembly of the procedure table is in a first tilted orientation relative to the vertical column.
Figure 3:
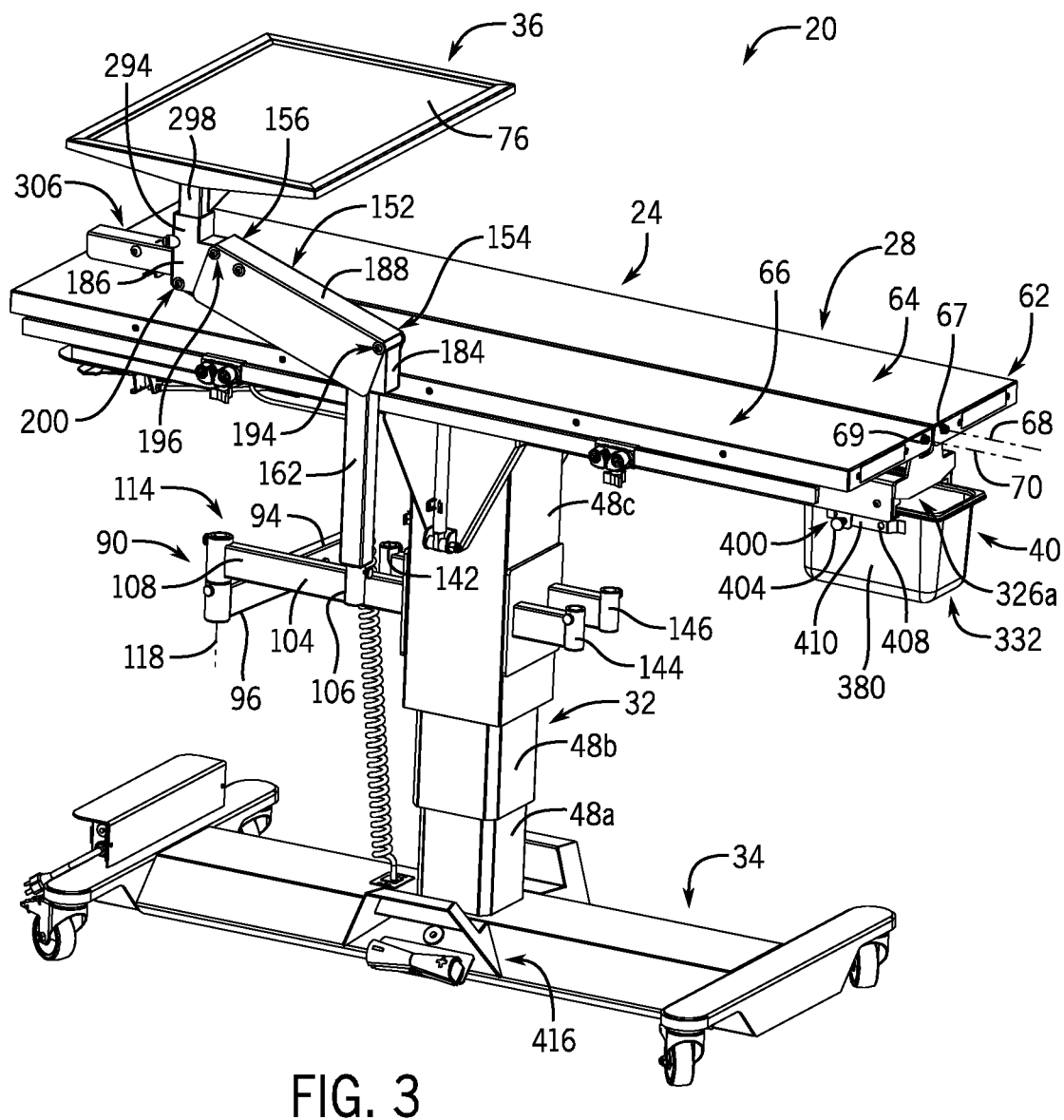
FIG. 3 shows an isometric view of the veterinary procedure table system of FIG. 1, wherein the back table is in the second circumferential position relative to the procedure table, wherein the animal support surface assembly of the procedure table is in a second height position relative to the base, and wherein the animal support surface assembly of the procedure table is in a first tilted orientation relative to the vertical column.
Figure 4:
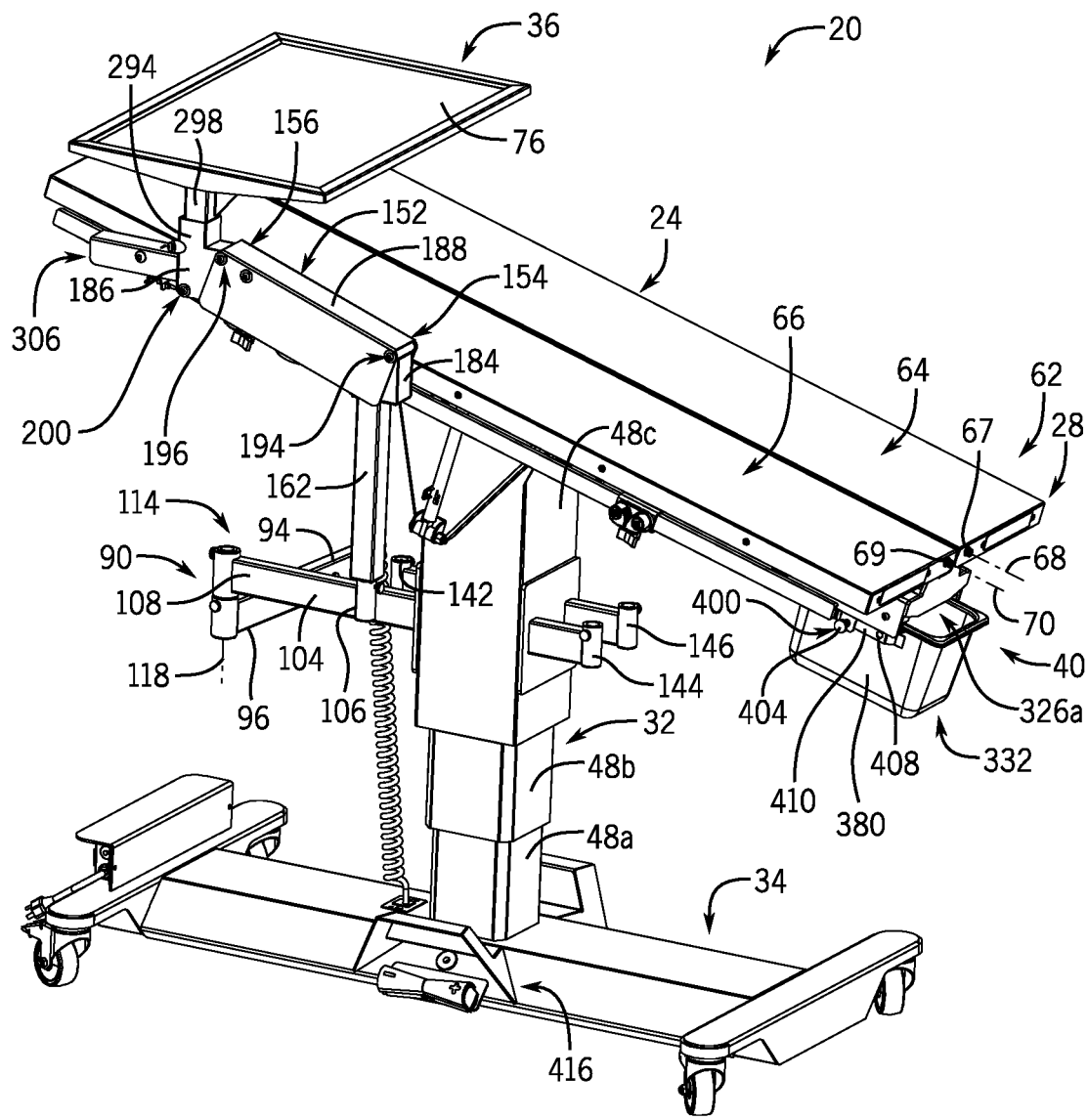
FIG. 4 shows an isometric view of the veterinary procedure table system of FIG. 1, wherein the back table is in the second circumferential position relative to the procedure table, wherein the animal support surface assembly of the procedure table is in a second height position relative to the base, and wherein the animal support surface assembly of the procedure table is in a second tilted orientation relative to the vertical column.

FIGS. 1-15 depict an exemplary embodiment of a veterinary procedure table system 20. The veterinary procedure table system 20 is generally configured for veterinary surgery or dental procedures, however it should be appreciated that the veterinary procedure table system 20 may be adapted for any suitable veterinary examination, treatment, and transport procedure, and accordingly, the term veterinary procedure table system should not be construed as limiting.

The veterinary procedure table system 20 generally includes a procedure table 24 having an animal support surface assembly 28 secured to a vertical column 32 that extends vertically from a base 34. The animal support surface assembly 28 is moveable between at least first and second animal support surface height positions relative to the base 34 as well as between at least first and second tilted orientations relative to the vertical column 32.

The veterinary procedure table system 20 further includes an integrated back table 36 for holding instruments and other supplies needed during the procedure. The back table 36 is secured to the procedure table 24 in a manner such that it is raised off the floor and compactly positioned next to the procedure table 24, thereby minimizing its footprint in the procedure room. The back table 36 is also configured to be optimally positioned near the procedure table 24. For instance, the back table 36 may be moved into various locations about the perimeter of the procedure table 24 as well as between at least first and second back table height positions. Moreover, the back table 36 is secured to the procedure table 24 such that the back table 36 moves up and down with the procedure table 24, yet the back table 36 does not tilt with the procedure table 24.

The animal support surface assembly 28 of the procedure table 24 is defined as a two panel V-top system 62 that adjusts from an elongated flat shape to an elongated V-shape to hold the patient in the desired position during surgery, as commonly used with prior art systems. However, unlike prior art systems, the veterinary procedure table system 20 includes a fluid collection and cleaning assembly 40 that allows for effectively collecting fluid beneath the V-top system, and that further allows for cleaning the channel beneath the V-top system without having to remove the channel.

These and additional aspects of the veterinary procedure table system 20 will become better understood by the description that follows.

Procedure Table

Referring to FIGS. 1, 3, 4, and 7, the procedure table 24 will first be described. It should be appreciated that many aspects of the procedure table 24 are well known, and therefore such aspects will not be described in detail. Moreover, it can be appreciated that although the embodiments of the veterinary procedure table system 20 are described and shown with reference to the procedure table 24, it should be appreciated that aspects of the veterinary procedure table system 20 may instead be used on procedure tables of different designs.

As briefly described above, the procedure table 24 includes an animal support surface assembly 28 secured to a vertical column 32. The vertical column 32 extends vertically and transversely from the base 34, which may be moveable against a floor surface, such as with casters.

As also briefly described above, the animal support surface assembly 28 is moveable between at least first and second animal support surface height positions as well as between at least first and second tilted orientations. Regarding the ability to move the animal support surface assembly 28 between at least first and second height positions, the vertical column 32 is configured to extend and retract to correspondingly raise or lower the animal support surface assembly 28 relative to the base 34.

In the depicted exemplary embodiment, the vertical column 32 is defined by an innermost, a middle, and an outermost telescoping vertical column extender 48*a*, 48*b*, and 48*c* that are moveable relative to each other to accommodate raising or lowering of the animal support surface assembly 28. The middle and outermost telescoping vertical column extenders 48*b* and 48*c* are moveable by a lifting mechanism (not shown), which may be at least partially housed within a hollow interior of the innermost vertical column extender 48*a*. Although the telescoping vertical column extenders 48*a*, 48*b*, and 48*c* may have any suitable cross-sectional shape, in the depicted exemplary embodiment, the telescoping vertical column extenders 48*a*, 48*b*, and 48*c* have a substantially square cross-sectional shape.

Regarding the ability to move the animal support surface assembly 28 between at least first and second tilted orientations, the procedure table 24 includes a tilt assembly 52 (not shown in detail) that pivotally couples the animal support surface assembly 28 to the vertical column 32. In this manner, the animal support surface assembly 28 can pivot relative to the vertical column 32 i.e., the animal support surface assembly can pivot between various angled positions relative to the vertical column. A suitable automatic or manual actuator may be used to pivot the animal support surface assembly 28 relative to the vertical column 32. For instance, referring to FIG. 12, a tilt lever assembly 444 (described below) may be used to release a lock, activate an actuator, etc., to move the animal support surface assembly 28 between at least the first and second tilted orientations.

The animal support surface assembly 28 of the procedure table 24 includes a two panel V-top system 62 that adjusts from an elongated flat shape to an elongated V-shape to hold the patient in the desired position during surgery. The two panel V-top system 62 includes first and second elongated leafs or panels 64 and 66 that are positioned substantially adjacent to one another and pivot along first and second elongated axes 68 and 70 between at least a first, substantially flat, co-planar position (see FIGS. 1-4) and a raised V-shape position (see FIG. 7). Any suitable automatic or manual actuator may be used to move the first and second elongated panels 64 and 66 between the first and second positions.

Back Table

Referring to FIGS. 1-6, the back table 36 for holding instruments and other supplies needed during a procedure will now be described. In general, the back table 36 includes a tabletop 76 that is moveably coupled to the vertical column 32 of the procedure table 24 through an articulating arm assembly 90 and a linkage assembly 152. The articulating arm assembly 90 secures the back table 36 to the procedure table 24 in a manner such that it is raised off the floor and compactly positioned next to the procedure table 24. Moreover, the articulating arm assembly 90 can be used to circumferentially position the back table 36 into one of various locations about the perimeter of the procedure table 24. Further, the articulating arm assembly 90 secures the back table 36 to the procedure table 24 such that the back table 36 moves up and down with the procedure table 24, yet the back table 36 does not tilt with the procedure table 24. The linkage assembly 152 is configured to position the tabletop 76 at various back table height positions while maintaining the tabletop 76 in a substantially horizontal orientation.

Referring specifically to FIGS. 1-4, the articulating arm assembly 90 will first be described. The articulating arm assembly 90 generally includes a plurality of armed segments that extend substantially horizontally from the vertical column 32 and that pivot relative to one another about substantially vertical pivot axes.

In the depicted embodiment, the articulating arm assembly 90 includes a first arm segment 94 having first and second ends 96 and 98 and a second arm segment 104 having first and second ends 106 and 108. The first end 96 of the first arm segment 94 is vertically offset from the second end 108 of the second arm segment 104 and pivotally coupled to the second end 108 of the second arm segment 104 through a first pivot joint 114. The first pivot joint 114, which may be any suitable design, allows the first and second arms segments 94 and 104 to pivot relative to one another about a first pivot axis 118 extending vertically through the first pivot joint 114.

At its second end, the first arm segment 94 is pivotally coupled to the outermost telescoping vertical column extender 48*c* of the vertical column 32 such that the articulating arm assembly 90 moves up and down with the outermost vertical column extender 48*c* and such that the articulating arm assembly 90 may pivot relative to the outermost vertical column extender 48*c*. In the depicted embodiment, the second end 108 of the first arm segment 94 is pivotally coupled to the outermost telescoping vertical column extender 48*c* through a second pivot joint 124. The second pivot joint 124, which may be any suitable design, allows the first arm segment 94 to pivot relative to the outermost telescoping vertical column extender 48c about a second pivot axis 128 extending vertically through the second pivot joint 124.

In one embodiment, the second pivot joint 124 is defined by a pin (not shown) extending transversely from the second end 108 of the first arm segment 94, i.e., along the second pivot axis 128, that is receivable within a first socket 134 secured to the outermost telescoping vertical column extender 48c of the vertical column 32. Preferably, the first socket 134 is spaced from the outermost telescoping vertical column extender 48c of the vertical column 32, such as with a horizontal member 138, to minimize any pinching hazard between the articulating arm assembly 90 and the vertical column 32.

Additional sockets, such as second, third, and fourth sockets 142, 144, and 146 may be located circumferentially around the outermost telescoping vertical column extender 48c of the vertical column 32 for pivotally receiving one or more additional back tables or other procedure accessories. In that regard, the pin at the second end 108 of the first arm segment 94 may be removably receivable within the first socket 134 such that it may be removed and instead inserted into one of the second, third, or fourth sockets 142, 144, and 146 to change the circumferential range of the back table 36.

With the articulating arm assembly 90 pivotally secured to one of the first, second, third, or fourth sockets 134, 142, 144, and 146, the back table 36 may be moved into one of various locations about the perimeter of the procedure table 24. More specifically, in the embodiment shown, the first arm segment 94 can pivot relative to the second arm segment 104 about the first pivot axis 118, and at the same time, the first arm segment 94 can pivot relative to the vertical column 32 about the second pivot axis 128. In this manner, the articulating arm assembly 90 facilitates movement of the back table 36 along are arced path around the perimeter of the procedure table 24, as well as in generally forward and backward directions closer to and farther away from the procedure table 24. The articulating arm assembly 90, therefore, provides multiple degrees of freedom for circumferentially positioning the back table 36 about the perimeter of the procedure table 24.

It should be appreciated that the first and/or second pivot joints 114 and 124 of the articulating arm assembly 90 may instead be defined as ball joints. By using a ball joint rather than a pivot joint, the articulating arm assembly 90 would additionally have the ability to position the back table 36 at various heights relative to the procedure table 24. However, in the embodiments described herein, a pivot joint over a ball joint is preferred for at least the reason that the linkage assembly 152 is configured to position the tabletop 76 at various height positions while providing the additional benefit of maintaining the tabletop 76 in a substantially horizontal orientation.

Figure 7:
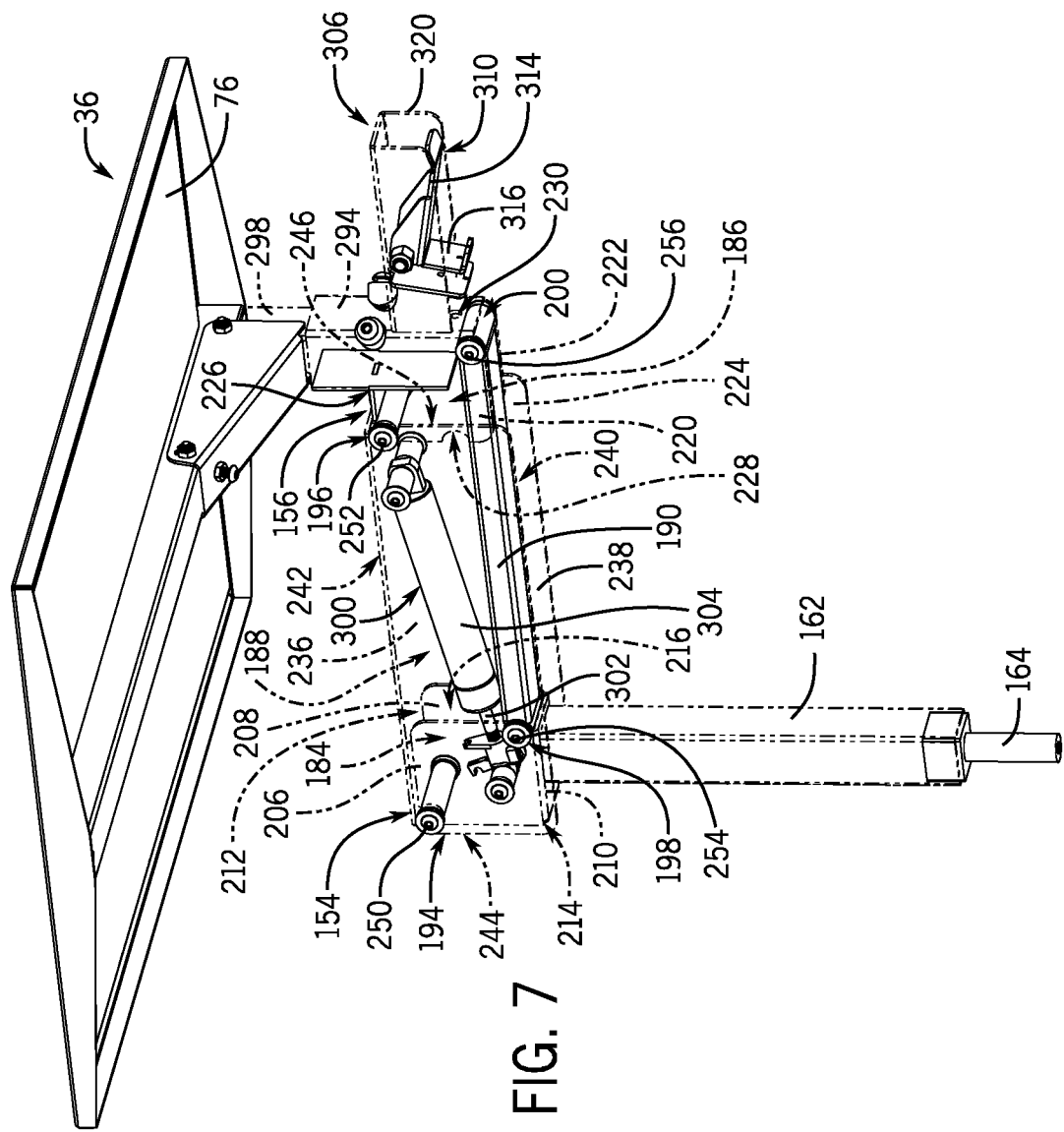
FIG. 7 shows an isometric view of the back table of FIG. 5, wherein the back table is in the first height position.

Referring additionally to FIGS. 5-7, the linkage assembly 152 will now be described. The linkage assembly 152 is located between the articulating arm assembly 90 and the tabletop 76 of the back table 36 to facilitate vertical movement of the tabletop 76 relative to the articulating arm assembly 90. In the depicted embodiment, a first elongated end 154 of the linkage assembly 152 is secured to the first end 106 of the second arm segment 104 of the articulating arm assembly 90 with a downwardly extending vertical offsetting member 162.

The vertical offsetting member 162 may be secured to the first end 106 of the second arm segment 104 in any suitable manner, such as by securing a pin 164 extending axially from a bottom end of the vertical offsetting member 162 (see FIG. 5) in a pin receptacle 166 (see FIG. 13) defined in the first end 106 of the second arm segment 104. The pin 164 may be secured within the pin receptacle 166 with a set screw, by press-fit, etc.

The vertical offsetting member 162 locates the tabletop 36 at a predefined height relative to the articulating arm assembly 90 such that when the linkage assembly 152 is in a lowered configuration (see FIG. 5), the tabletop 36 is at a first back table height position relative to the procedure table 24. The first back table height may be a typical height used, for instance, when the procedure table 24 is in a lowered procedure table height position and/or a non-tilted orientation. The linkage assembly 152 can be used to raise the tabletop 36 from the first back table height position to at least a raised back table height position (see FIG. 6) when, for instance, the procedure table 24 is in a raised procedure table height position and/or a tilted orientation. Thus, the linkage assembly 152 facilitates movement of the tabletop 76 between at least the lowered back table height configuration (FIG. 5) and the raised back table height position (FIG. 6) to accommodate the procedure table configuration and/or the logistical setup of the procedure room.

Referring specifically to FIGS. 5 and 6, the linkage assembly 152 is depicted as a 4-bar kinematic linkage having a first link 184, a second link 186, a third link 188, and a fourth link 190 pivotally coupled together by first, second, third, and fourth pivot assemblies 194, 196, 198, and 200. The first and second links 184 and 186 are located at first and second opposite elongated ends 154 and 156 of the linkage assembly 152, and the third and fourth links 198 and 200 extend between and are pivotally coupled to the first and second links 184 and 186.

In the depicted embodiment, the first link 184 is a generally a hollow, open rectangular-shaped member defined by a first lateral side 206 opposite a second lateral side 208, a bottom side 210 opposite a top open side 212, and a rear side 214 opposite a front open side 216. The bottom side 210 of the first link 184 is secured to an upper end of the vertical offsetting member 162 such that the first link 184 remains fixed in orientation as the linkage assembly 152 moves the tabletop 36 between the raised and lowered positions.

The second link 186 is substantially identical in configuration to the first link 184, although in an inverted orientation. In that regard, the second link 186 is a generally a hollow, open rectangular-shaped member defined by a first lateral side 220 opposite a second lateral side 222, a bottom open side 224 opposite a top side 226, and a rear side 228 opposite a front side 230. A tabletop mounting member 294 extends upwardly from the top side of the second link 186 for connecting the second link 186, and therefore the second elongated end 156 of the linkage assembly 152 to the tabletop 36 in a suitable manner. For instance, a post 298 extending vertically downwardly from a bottom surface of the tabletop 36 may be (optionally removably) received within a receptacle in the tabletop mounting member 294.

The third link 188 is an elongated U-shaped member defined by a first lateral side 236 opposite a second lateral side 238, a bottom open side 240 opposite a top side 242, and a rear open side 244 opposite a front open side 246. The first and second links 184 and 186 are at least partially nested within the rear and front open sides 244 and 246 of the third link 188 as the linkage assembly 152 is moved between raised and lowered configurations. More specifically, in the lowered configuration shown in FIG. 5 with the third link 188 substantially transverse to the vertical offsetting member 162, the first link 184 is fully nested within the rear open side 244 of the third link 188. At the same time, the second link 186 is only partially nested within the front open side 246 of third link 188. As the linkage assembly 152 moves toward the raised configuration shown in FIG. 6, the first and second links 184 and 186 move toward a mirrored nesting configuration within the third link 188.

The fourth link 190 is an elongated tubular member that extends between and is pivotally coupled to the first and second links 184 and 186. The fourth link 190 nests within the bottom open side 240 of the third link 188. The fourth link 190 also selectively nests within the first and second links 184 and 186 as the linkage assembly 152 is moved between raised and lowered configurations. Referring to FIG. 5, the fourth link 190 nests within the bottom open side 224 of the second link 184 when the linkage assembly 152 is in the lowered configuration. As the linkage assembly 152 moves toward the raised configuration, as shown in FIG. 6, the fourth link 190 moves towards a nested configuration within the front open side 216 of the first link 184. In that regard, the fourth link 190 may be rectangular in shape to suitably nest within the rectangular-shaped first, second, and third links 184, 186 and 188.

As the linkage assembly 152 is moved between lowered and raised configurations, the first, second, and fourth links 184, 186, and 190 move into and out of at least a partially nested configuration within the third link 188. In other words, the U-shaped interior of the third link 188 always at least partially encapsulates the first, second, and fourth links 184, 186, and 190. Prior art 4-bar linkage assemblies have an open structure so the gap between links decreases as the linkage assembly moves into various configurations, creating a pinch hazard. The linkage assembly 152 described and shown herein minimizes or eliminates any gaps between the links.

The first, second, third, and fourth pivot assemblies 194, 196, 198, and 200 pivotally connect the first, second, third and fourth links 184, 186, 188, and 190 such that the links may pivot relative to each other to raise and lower the tabletop 76 while substantially maintaining the tabletop 76 in a horizontal position. In general, the third link 188 extends between and is pivotally coupled to the first and second links 184 and 186 through the first and second pivot assemblies 194 and 196, respectively. Moreover, the fourth link 190 extends between and is pivotally coupled to the first and second links 184 and 186 through third and fourth pivot assemblies 198 and 200, respectively.

More specifically, the first pivot assembly 194 pivotally couples the first link 184 to the third link 188 with a first pin 250. The first pin 250 passes transversely through the first and second lateral sides 206 and 208 of the first link 184 at a first corner 260 defined by the rear side 214 and the top open side 212 of the first link 184. The first pin 250 also passes transversely through the first and second lateral sides 236 and 238 of the third link 188 at a first corner 262 defined by the rear open side 244 and the top side 242 of the third link 188.

The second pivot assembly 196 pivotally couples the second link 186 to the third link 188 with a second pin 252. More specifically, the second pin 252 passes transversely through the first and second lateral sides 220 and 222 of the second link 186 at a first corner 264 defined by the rear open side 228 and the top side 226 of the second link 186. The second pin 252 also passes transversely through the first and second lateral sides 236 and 238 of the third link 188 at a second corner 266 defined by the front open side 244 and the top side 242 of the third link 188.

The third pivot assembly 198 pivotally couples the first link 184 to the fourth link 190 with a third pin 254. More specifically, the third pin 254 passes transversely through the first and second lateral sides 206 and 208 of the first link 184 at a second corner of the first link 184 diametrically opposite the first corner 260. The third pin 254 also passes transversely through a first end 274 of the fourth link 190.

Finally, the fourth pivot assembly 200 pivotally couples the second link 186 to the fourth link 190 with a fourth pin 256. More specifically, the fourth pin 256 passes transversely through the first and second lateral sides 220 and 222 of the second link 186 at a second corner of the second link 86 diametrically opposite the first corner 264. The fourth pin 256 also passes transversely through a second end 276 of the fourth link 190 opposite the first end 274. A bushing or other low-friction member (not labeled or shown in detail) may be disposed between the links and the corresponding pins to help facilitate easy movement of the linkage assembly 152.

The first, second, third, and fourth pivot assemblies 194, 196, 198, and 200 are in a parallelogram arrangement within the linkage assembly 152. Moreover, the distance between the first and second pivot assemblies 194 and 196 remains fixed, the distance between the third and fourth pivot assemblies 198 and 200 remains fixed, the distance between the first and third pivot assemblies 194 and 198 remains fixed, and the distance between the second and fourth pivot assemblies 196 and 200 remains fixed. As a result, the first, second, third, and fourth pivot assemblies 194, 196, 198, and 200 are in a first parallelogram arrangement when the tabletop 76 is in the lowered configuration (FIG. 5). As the tabletop 76 is moved from the lowered configuration into, the raised configuration (FIG. 6), the first, second, third, and fourth pivot assemblies 194, 196, 198, and 200 shift into a mirrored, second parallelogram arrangement. The shift of the first, second, third, and fourth pivot assemblies 194, 196, 198, and 200 from the first parallelogram arrangement into the mirrored, second parallelogram arrangement moves the second link 186, and therefore the tabletop 76 along an arced upward path until it reaches the raised configuration.

As the first, second, third, and fourth pivot assemblies 194, 196, 198, and 200 shift from the first parallelogram arrangement into the mirrored, second parallelogram arrangement, the distance between the first and second pivot assemblies 194 and 196 remains fixed, the distance between the third and fourth pivot assemblies 198 and 200 remains fixed, the distance between the first and third pivot assemblies 194 and 198 remains fixed, and the distance between the second and fourth pivot assemblies 196 and 200 remains fixed. As a result, the second link 186 remains in a substantially horizontal orientation as it travels along the arced upward path toward the raised configuration. Therefore, the tabletop 76, which is secured to the second link 186, remains in a substantially horizontal orientation as it is raised.

It can be appreciated that the second link 186 and the tabletop 76 also remain in a substantially horizontal orientation as they are lowered when the first, second, third, and fourth pivot assemblies 194, 196, 198, and 200 shift from the second parallelogram arrangement into the first parallelogram arrangement. Of note, the interior of the top side 242 of the third link 188 abuts against the exterior of the top open side 212 of the first link 184 to prevent the third link 188 from moving past the lowered configuration shown in FIG. 5.

To assist in moving the linkage assembly 152 between the lowered configuration and the raised configuration, the back table 36 further includes an actuator or biasing mechanism. In the depicted exemplary embodiment, the back table 36 includes a gas strut 300 having a piston 302 extendable within a pressurized (i.e., gas-charged or preloaded) cylinder 304. The proximal end of the cylinder 304 is pivotally coupled to the first and second lateral sides 236 and 238 of the third link 188 through a pivot pin (not labeled) extending transversely therethrough, and the distal end of the piston 302 is pivotally coupled to the first and second lateral sides 206 and 208 of the first link 184 through a pivot pin (not labeled) extending transversely therethrough.

When the linkage assembly 152 is in the lowered configuration as shown in FIG. 5, the gas strut 300 is in a retracted, loaded configuration. When the linkage assembly 152 is moved into the raised configuration as shown in FIG. 6, the gas strut 300 moves into an extended configuration. The preload of the gas strut 300 is suitable to provide direct support for safely and more easily lifting, positioning, lowering and counterbalancing the weight of the tabletop 76 and its supporting structure.

The gas strut 300 is lockable in any stroke position (e.g., an extended, retracted, partially extended, or partially retracted position) through a releasable locking assembly 306. The releasable locking assembly 306 includes a release lever assembly 310 operably connected to a lock on the gas strut 300. For instance, the release lever assembly 310 may include a release lever 314 having a grasping portion 314 transverse to a cable attachment portion 316, wherein the release lever 314 is pivotally secured to the interior of a lever mount 320 extending from the tabletop mounting member 294. When the grasping portion 314 is depressed, the release lever 314 pivots about a pivot pin (not labeled) to correspondingly move the cable attachment portion 316. The cable attachment portion 316 is attached to a lock on the gas strut 300 through a cable (not shown) to selectively unlock the gas strut 300, thereby allowing the tabletop 76 to be raised and lowered.

The lever mount 320 may define a contoured area on which a portion of the user's hand may rest when depressing the grasping portion 314 of the release lever 314. For instance, in the depicted embodiment, the lever mount 320 is an elongated U-shape having a bottom and front opening to provide access to the release lever 314. Any other suitable shape or configuration may instead be used.

As can be appreciated from the foregoing, the back table 36 is secured to the procedure table 24 in a manner such that it is raised off the floor and compactly positioned next to the procedure table 24, thereby minimizing its footprint in the surgery or procedure room. The back table 36 is also configured to be optimally positioned near the procedure table 24 by moving the back table 36 into various locations about the perimeter of the procedure table 24 as well as between at least first and second back table height positions while maintaining the tabletop in a substantially horizontal orientation. Moreover, the back table 36 is secured to the procedure table 24 such that the back table 36 moves up and down with the procedure table 24, yet the back table 36 does not tilt with the procedure table 24.

Fluid Collection and Cleaning Assembly

The fluid collection and cleaning assembly 40 that allows for easy cleaning of a channel beneath the first and second panels 64 and 66 of the animal support surface assembly 28, and that further allows for effectively collecting fluid beneath the animal support surface assembly 28 will now be described with reference to FIGS. 8-10. Aspects of the fluid collection and cleaning assembly 40 that allows for easy cleaning of a channel beneath the first and second panels 64 and 66 of the animal support surface assembly 28 will first be described.

In a first aspect, the fluid collection and cleaning assembly 40 includes first and second pivot plates 326a and 326b that elevate first and second ends of the first and second elongated panels 64 and 66 above an elongated collection channel for better access to the channel for cleaning. In a second aspect, the fluid collection and cleaning assembly 40 includes a contoured or recessed bottom surface defined on the first and second elongated panels 64 and 66 to facilitate easier access to the channel 330.

The first and second pivot plates 326a and 326b that elevate first and second ends of the first and second panels 64 and 66 above the channel 330 for better access to the channel for cleaning will now be described. The first and second pivot plates 326a and 326b are identical, and therefore, only the first pivot plate 326a will be described.

The first pivot plate 326a includes a base portion 334 that extends across and substantially encloses an open end of the channel 330. First and second pivot portions 336 and 338 extend upwardly from the base portion 334 and are configured to pivotally receive pins (not labeled) of first and second pivots 67 and 69 of the first and second elongated panels 64 and 66, respectively. The first and second pivot portions 336 and 338 are spaced apart a sufficient distance to allow the first and second elongated panels 64 and 66 to pivot about the first and second pivot axes 68 and 70 between the elongated flat shape and the elongated V shape and so as to define the gap 72 between the elongated panels 64 and 66 according to industry standards.

Moreover, the first and second pivot portions 336 and 338 extend upwardly from the base portion 334 to elevate the elongated panels 64 and 66 above the channel 330 for cleaning the channel. More specifically, the first pivot plate 326a locates the elongated panels 64 and 66 a sufficient height above the channel 330 such that a typical user's hand may easily fit in the gap between the panels 64/66 and the channel 330. In this manner, the user may access the channel 330 for cleaning the channel, such as with a sponge, vacuum, etc., without removing the channel from the procedure table 24.

As noted above, the first and second elongated panels 64 and 66 include a contoured or recessed bottom surface to facilitate greater access to the channel 330. For instance, the bottom surface of each elongated panel 64 and 66 may be recessed near its bottom, inner elongated edge 366 to increase the gap between the panel and the channel 330. In the depicted exemplary embodiment, the first elongated panel 64 includes a first elongated panel support 340 secured to the underside of the first panel, which can help stiffen the first panel 64 to better support the weight of an animal during a procedure. The first elongated panel support 340 extends between an outer elongated edge of the first elongated panel 64 toward an inner elongated edge of the first elongated panel 64 (not labeled in FIG. 9). The first elongated panel support 340 includes a first inner elongated edge 341 that is at least one of curved, tapered, or recessed to increase the distance between the underside of the first elongated panel 64 and the elongated channel 330.

In the depicted embodiment, the first inner elongated edge 341 is curved to increase the gap between the underside of the first elongated panel 64 and the channel 330 near the inner elongated edge of the first elongated panel 64, thereby providing more space for a user's hand or cleaning equipment. A curved first inner elongated edge 341, versus an edge with sharper edges, may also be easier to clean when the underside of the panel becomes soiled from fluid that splashes up from the channel. The first inner elongated edge 341 of the first elongated panel support 340 may also be spaced from the inner elongated edge of the first elongated panel 64, as shown, to increase the gap between the underside of the first elongated panel 64 and the channel 330 near the inner elongated edge of the first elongated panel 64.

The second elongated panel 66 may similarly include a second elongated panel support 342 secured to the underside of the second panel. The second elongated panel support 342 is identical to the first elongated panel support 340. In that regard, the second elongated panel support 342 includes a curved second inner elongated edge 341 that facilitates improved access on the side of the channel 330 beneath the second elongated panel 66. It can be appreciated that the contoured or recessed inner elongated edges of the elongated panel supports 340 and 342, combined with the fact that the panels 64 and 66 are elevated above the channel 330, allow for better access to the channel 330 for cleaning.

Aspects of the fluid collection and cleaning assembly 40 that allow for effectively collecting fluid beneath the animal support surface assembly 28 will now be described. In a first aspect, the fluid collection and cleaning assembly 40 includes a contoured elongated collection channel 330 (or simply, "channel 330") that is specially-designed to minimize fluid splash as the fluid flows downwardly from the elevated panels 64 and 66. In a second aspect, the fluid collection and cleaning assembly 40 includes a catchment assembly 332 for collecting fluid when the animal support surface assembly is in at least first and second tilted orientations or other configurations. In a third aspect, the fluid collection and cleaning assembly 40 includes a fluid flow directing assembly 362 configured to help direct the flow of fluid into the channel 330.

The contoured elongated collection channel 330 specially-designed to minimize fluid splash from the elevated panels 64 and 66 will first be described. As noted above, by elevating the first and second panels 64 and 66 above the channel 330, the fluid flowing off the panels 64 and 66 (e.g., through the gap 72) and down into the channel can splash up and out of the channel. In that regard, the channel 330 has a specially designed cross-sectional shape to minimize fluid splash.

Figure 8:
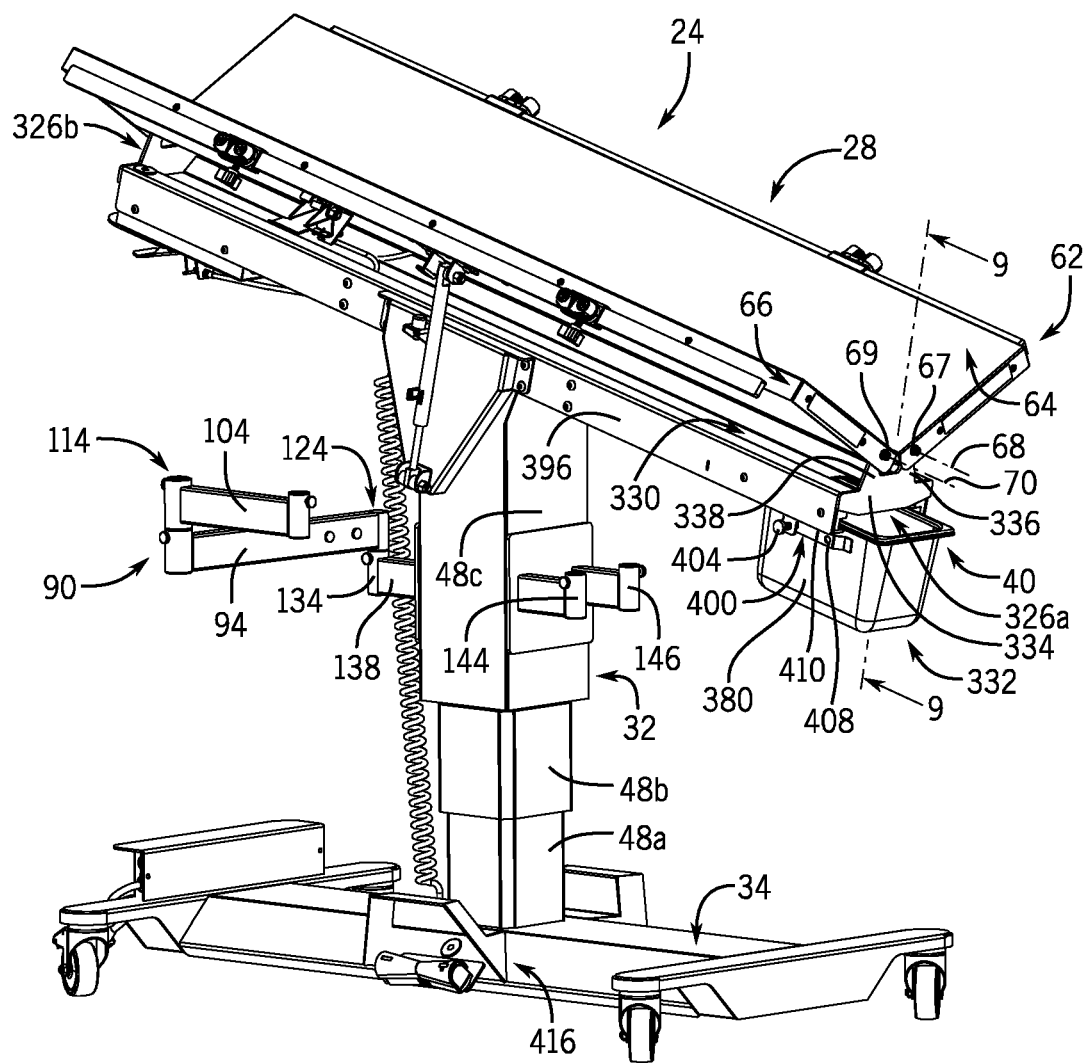
FIG. 8 shows an isometric view of the veterinary procedure table system of FIG. 1 having the back table removed, wherein the animal support surface assembly is in a V-shape configuration.
Figure 9:
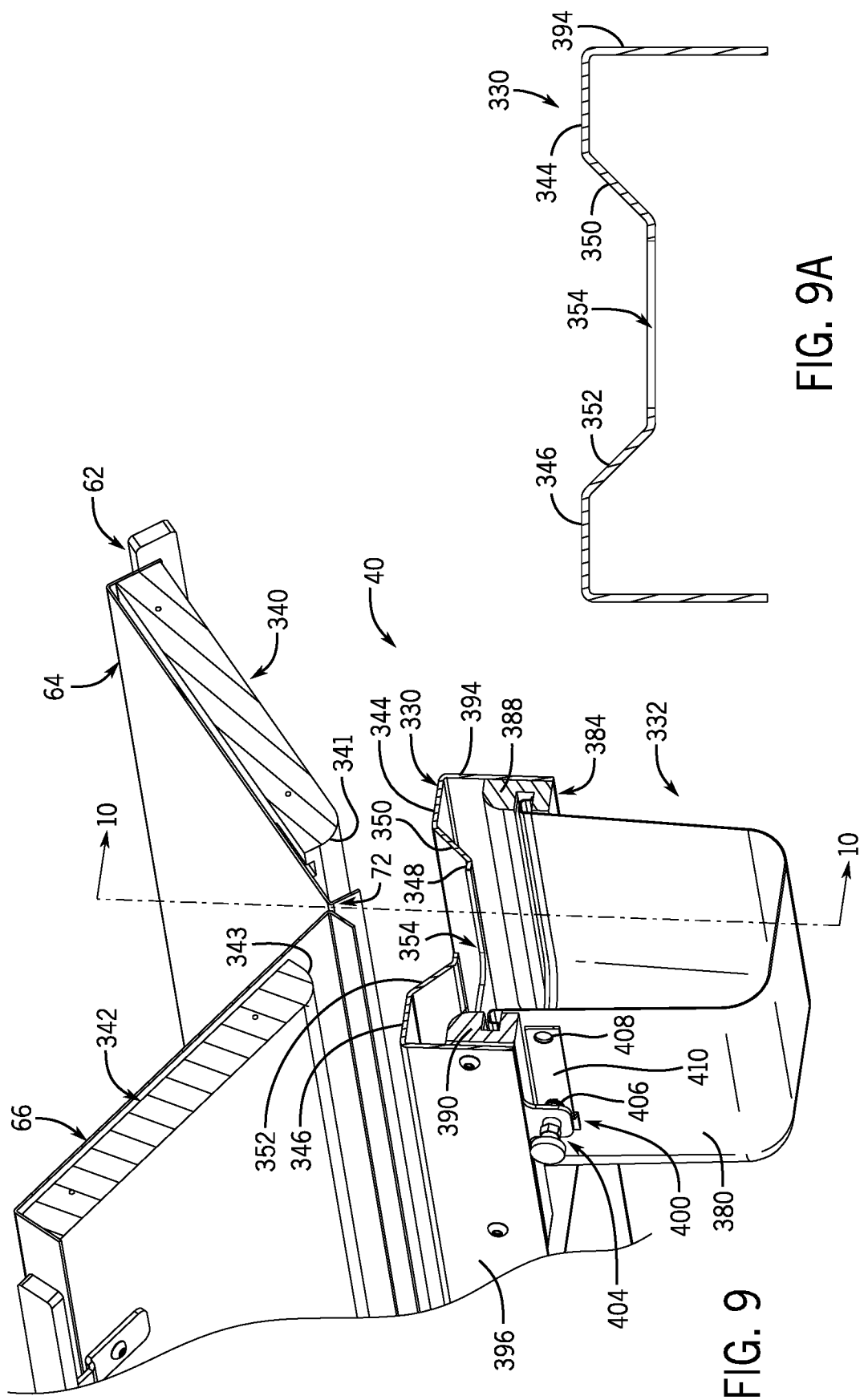
FIG. 9 shows an isometric cross-sectional view of a portion of the animal support surface assembly of FIG. 8, taken substantially across line 9-9.
Figures 10, 10A:
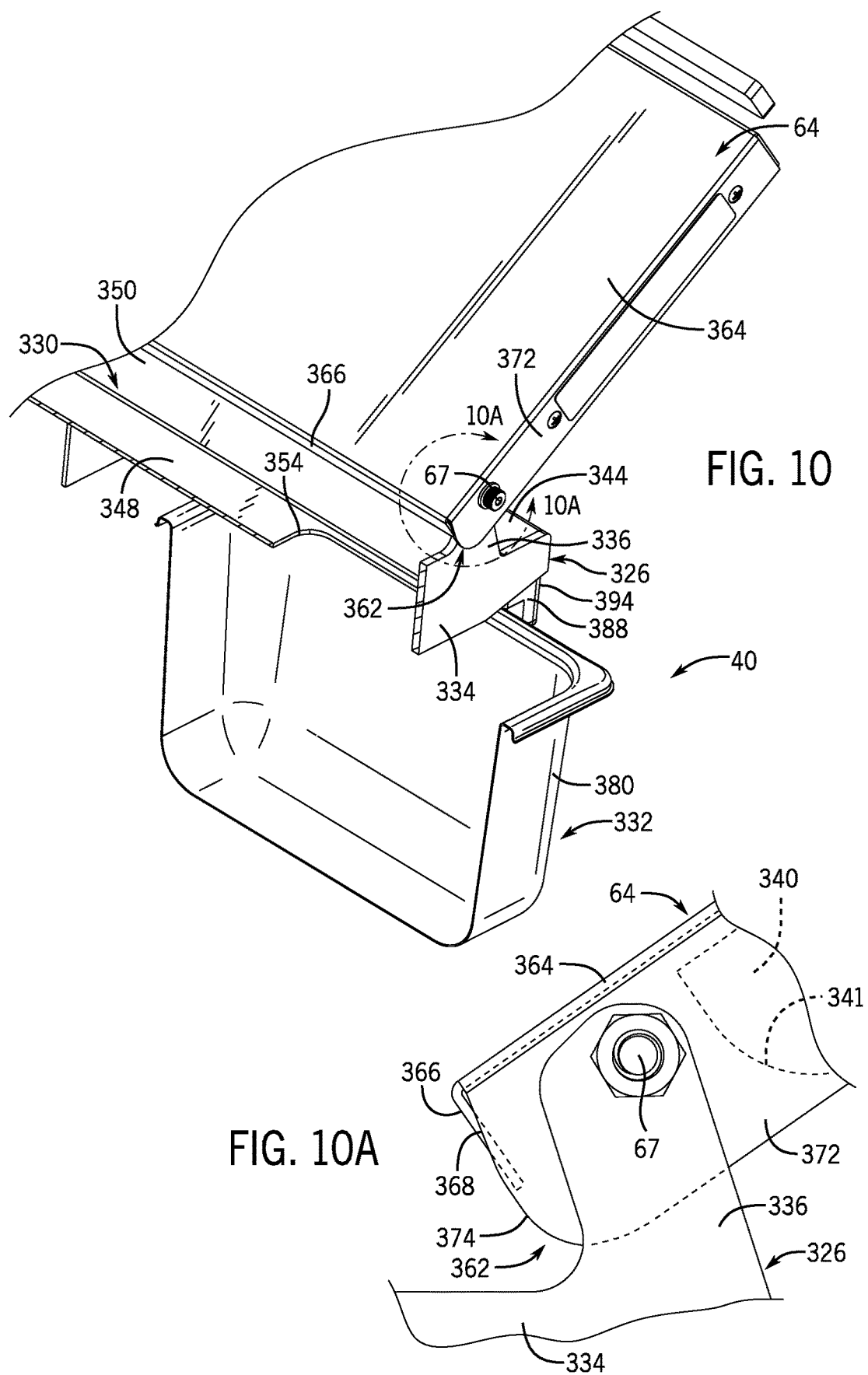
FIG. 10 shows an isometric cross-sectional view of a portion of the animal support surface assembly of FIG. 9, taken substantially across line 10-10.
FIG. 10A shows an isometric zoomed-in view of a fluid flow directing assembly of the veterinary procedure table system of FIG. 10.

Referring to FIGS. 8-10, the channel 330 extends along the length of the procedure table 24 beneath the gap 72 defined between the first and second panels 64 and 66. The cross-sectional shape of the channel 330 is substantially symmetrical about an axis transverse to the length of the channel 330. The channel 330 generally has a flattened "M" cross-sectional shape.

More specifically, the channel 330 includes a first lateral portion 344 extending from a first outer edge of the channel 330 across a portion of the width of the channel 330 towards the center of the channel. A substantially identical second lateral portion 346 is defined opposite the first lateral portion 344. In that regard, the second lateral portion 346 extends from a second outer edge of the channel 330 across a portion of the width of the channel 330 towards the center of the channel. The first and second lateral portions 344 and 346 are substantially co-planar and extend along a plane substantially parallel to a center longitudinal axis of the channel 330.

The channel 330 further includes a recessed middle portion 348 extending along substantially the center of the channel 330 between the first and second lateral portions 344 and 346. The middle portion 348 is recessed from the first and second lateral portions 344 and 346, i.e., in a lowered plane compared to the first and second lateral portions 344 and 346. The middle portion 348 also extends along plane substantially parallel to the plane of the first and second lateral portions 344 and 346. The width of the middle portion 348 is about equal to the combined width of the first and second lateral portions 344 and 346.

The channel 330 further includes a first angled portion 350 extending downwardly from the first lateral portion 344 to the recessed middle portion 348 and a mirrored second angled portion 352 extending downwardly from the second lateral portion 344 to the recessed middle portion 348. The first and second angled portions 350 and 352 extend downwardly from the first and second lateral portions 344 and 348 at an angle of about forty-five degrees (45°) and each have a width about equal to the width of the first and second lateral portions 344 and 346, respectively.

The channel 330 is positioned beneath the first and second elongated panels 64 and 66 such that the center longitudinal axis of the channel 330 is substantially aligned with the gap 72 between the panels 64 and 66. In this manner, fluid flows from the top of the panels 64 and 66, into the gap 72 defined between the elongated panels 64 and 66, and down into the recessed middle portion 348 of the channel 330. When the fluid flows down into the recessed middle portion 348 of the channel 330, it may splash up due to the height of the panels 64/66 relative to the channel 330. However, the fluid splash is substantially contained by the first and second angled portions 350 and 352 extending along each side of the recessed middle portion 348.

More specifically, the fluid splashes up from the recessed middle portion 348 and onto the first and second angled portions 350 and 352, but then flows back down along the first and second angled portions into the recessed middle portion 348. The fluid is collected in the recessed middle portion 348 and thereafter drained into the catchment assembly 332.

The catchment assembly 332 for collecting fluid when the animal support surface assembly is in at least first and second tilted orientations or other configurations will now be described. The catchment assembly 332 includes a bucket 380 secured beneath a drain opening 354 in the channel 330. The drain opening 354 is defined at a front of the recessed middle portion 348 and may be smaller in size than the opening of the bucket 380 such that the bucket can catch substantially all the fluid flowing out of the drain opening 354.

The bucket 380 may be moveable between at least first and second catch positions to accommodate, for instance, at least first and second tilt orientations of the animal support surface assembly 28. In that regard, the bucket 380 is slidably received within a slide assembly 384 defined by a first slide 388 positioned opposite a second slide 390. The first slide 388 is secured to an interior surface of a first channel edge 394 extending downwardly from the first lateral portion 344 of the channel 330, and the second slide 390 is secured to an interior surface of a second channel edge 396 extending downwardly from the second lateral portion 346 of the channel 330.

The catchment assembly 332 includes a bucket locating assembly 400 for securing the bucket 380 in a first catch position, such as when the table is in a first tilted orientation, i.e., with the animal support surface assembly 28 perpendicular to the vertical column 32, as shown in FIG. 8. In the first catch position, the bucket 380 is fully recessed within the slide assembly 384 and substantially aligned with the drain opening 354. The fluid flows directly downwardly from the panels 64/66 into the channel 330 and thereafter into the bucket 380.

Figure 13:
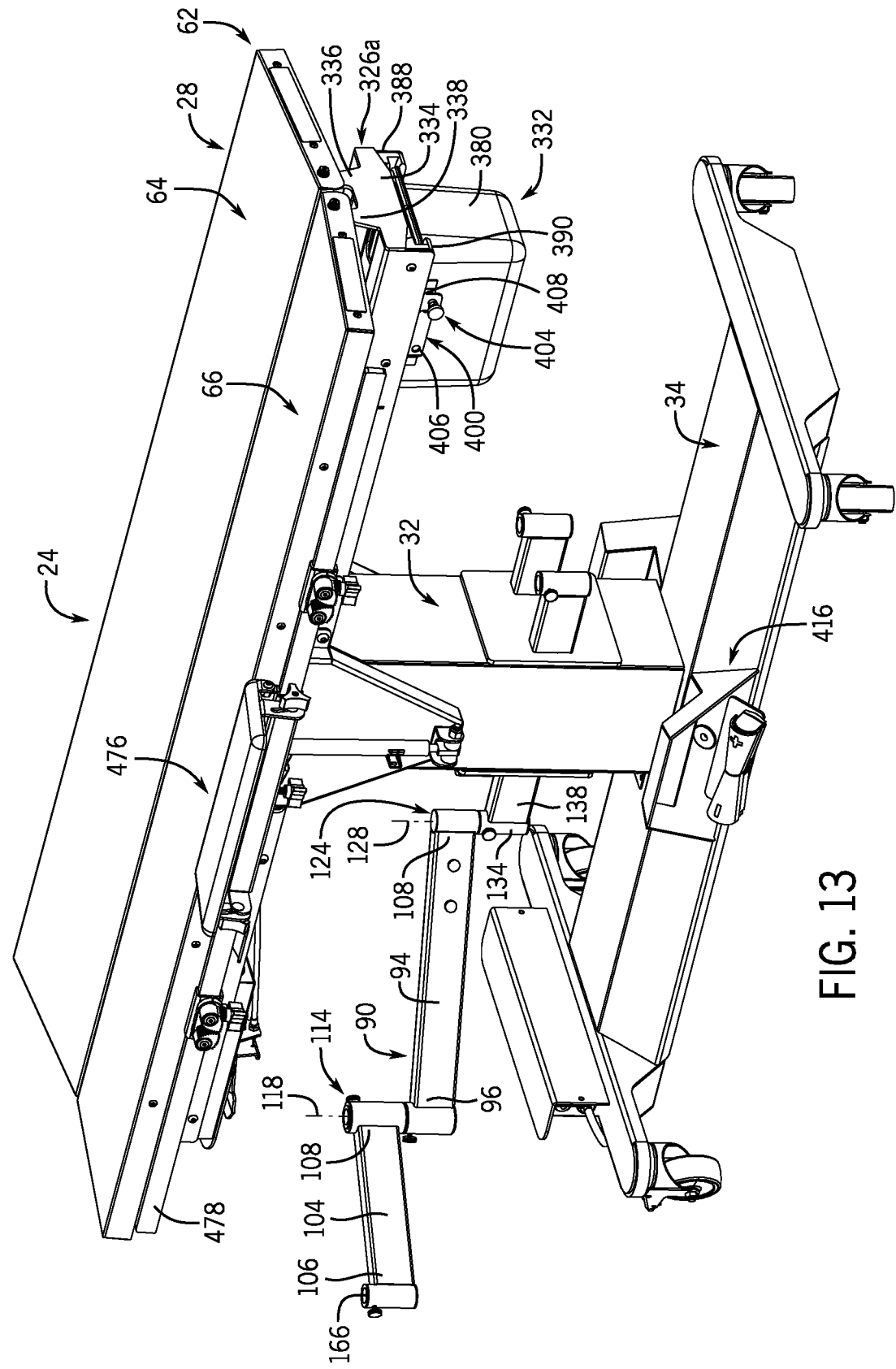
FIG. 13 shows an isometric view of the veterinary procedure table system of FIG. 1 having the back table removed, and further showing an arm rest assembly attached to a rail of the animal support surface assembly.

The bucket locating assembly 400 is also configured to secure the bucket 380 in a second catch position, such as when the table is in a second tilted orientation, i.e., with the animal support surface assembly 28 angled relative to the vertical column 32, as shown in FIG. 13. In the second catch position, the bucket 380 protrudes partially from the end of the slide assembly 384 and is forward of the drain opening 354. With the bucket 380 positioned forwardly of the drain opening 354, the bucket can catch the fluid as it flows downwardly from the panels 64/66 and into the angled channel 330 and thereafter downwardly and forwardly into the bucket 380. It should be appreciated that the first and second catch positions of the bucket 380 may also be used for other procedure table configurations or applications.

The bucket locating assembly 400 may be able suitable configuration for securing the bucket 380 in at least the first and second catch positions. In the depicted embodiment, the bucket locating assembly 400 includes a spring-loaded pin 404 secured to the second channel edge 396 that is receivable within at least one of first and second openings 406 and 408 defined in an elongated bracket 410 secured to the bucket 380. The spring-loaded pin 404 is received within the first opening 406 when the bucket 380 is in the first catch position fully recessed within the slide assembly 384. The spring-loaded pin 404 is received within the second opening 408 when the bucket 380 is in the second catch position partially protruding from the end of the slide assembly 384. The elongated bracket 410 may instead or additionally include any other openings to locate the bucket 380 in any other desired catch positions.

The fluid flow directing assembly 362 configured to help direct the flow of fluid into the channel 330 will now be described with reference to FIGS. 10 and 10A. In order to best understand aspects of the fluid flow directing assembly 362, the general flow of fluid from the panels 64 and 66 into the channel 330 will first be described.

In general, the fluid flows downwardly along a top face 364 of each panel 64 and 66, downwardly into the gap 72 (see FIG. 9), and then downwardly into the channel 330. When flowing off the top surface 364 of each panel 64 and 66 and through the gap 72, the fluid sometimes flows along a downwardly-turned elongated side face 366 that extends along the interior side of each panel 64 and 66 (labeled only on panel 64 in FIG. 10). As the fluid flows over the downwardly-turned elongated side face 366, most of the fluid flows straight down into the channel 330. However, some of the fluid flows forwardly toward a front edge 368 of the downwardly-turned elongated side face 366. The fluid can sometimes flow forwardly of the front edge 368 and onto the floor or surrounding areas of the procedure table 24. In that regard, the fluid flow directing assembly 362 is configured to trip the flow of the fluid and prevent the fluid from flowing forwardly of the front edge 368.

In the depicted exemplary embodiment, the fluid flow directing assembly 362 is defined by an overlap of the downwardly-turned elongated side face 366 and a downwardly-turned front face 372 of each panel 64 and 66 (shown only on panel 64 in FIG. 10A). As can be seen in FIG. 10A, the downwardly-turned elongated side face 366 extends substantially transversely from the top face 364 of panel 64. Moreover, the downwardly-turned front face 372 extends substantially transversely from the top face 364 of panel 64 and is also substantially transverse to the downwardly-turned elongated side face 366. In prior art systems, a V-top panel is formed such that a side edge of the downwardly-turned front face is flushed with or slightly recessed from a front edge of the downwardly-turned elongated side face (such as using standard sheet metal forming procedures). In the panel 64 of procedure table 24, the side edge 374 of the downwardly-turned front face 372 protrudes outwardly at least in part from the front edge 368 of the downwardly-turned elongated side face 366. In other words, at least a portion of the front edge 368 is tucked behind the side edge 374. The protruding side edge 374 of the downwardly-turned front face 372 helps trip the flow of the fluid and substantially prevents the fluid from flowing forwardly of the front edge 368.

The side edge 374 of the downwardly-turned front face 372 sits proud of the front edge 368 of the downwardly-turned elongated side face 366 near the bottom or distal end of the front edge 368, such as near the bottom one-third of the front edge 368. The side edge 374 of the downwardly-turned front face 372 has any suitable contour to sit proud of the distal end of the front edge 368. For instance, in the depicted exemplary embodiment, the front edge 368 extends gradually downwardly and outwardly from the top face 364 of the panel toward a bottom edge (not labeled) of the downwardly-turned front face 372. The corner defined between the front edge 368 and the bottom edge of the downwardly-turned front face 372 may be rounded to prevent anything from catching on the protruding portion of the downwardly-turned front face 372.

With the front edge 368 protruding only near the bottom edge of the downwardly-turned front face 372, the front edge 368 of the first panel 64 does not engage or otherwise interfere with the protruding front edge of the second panel 66. Accordingly, any pinching hazard between the front edges of the first and second panels 64 and 66 is minimized. At the same time, the side edge 374 of the downwardly-turned front face 372 protrudes sufficiently from the distal end of the front edge 368 to substantially prevent fluid from flowing forwardly of the front edge 368 of each panel.

Based on the foregoing, it can be appreciated that the fluid collection and cleaning assembly 40 allows for easy cleaning of the channel 330 beneath the first and second panels 64 and 66, and further allows for effectively collecting fluid beneath the animal support surface assembly 28.

Foot Switch Roof

Referring to FIGS. 11 and 11A, the veterinary procedure table system 20 may further include a foot switch assembly 416 having a foot switch 420 secured to the base 34 and operably coupled to certain functional features of the procedure table 24 (not shown). Prior art systems may use plastic bags taped around the foot switch 420 to prevent the foot switch 420 and any internal electrical components from being damaged from fluid or other debris.

In the depicted exemplary embodiment, the foot switch assembly 416 includes a foot switch roof 416 configured to cover and/or protect a foot switch 420 of the procedure table 24. The foot switch roof 416 is secured to or otherwise formed on the base 34 and extends upwardly and outwardly from the base 34 to shelter the foot switch 420. In that regard, the foot switch roof 416 includes an open-sided base portion 426 that extends upwardly and outwardly from the base 34, and an open-sided roof portion 428 that extends upwardly and outwardly from the base portion 426. Although the foot switch roof 416 may be any suitable shape, in the depicted exemplary embodiment, the base portion 426 is generally an open-sided triangular prism shape, and the roof portion 428 is generally an open-sided trapezoidal prism shape.

The base portion 426 and roof portion 428 extend outwardly from the base 34 a sufficient distance such that the roof portion 428 helps prevent fluid and other debris from reaching the foot switch 420. The base portion 426 and roof portion 428 also extend outwardly from the base 34 a sufficient distance such that a gap is defined between the roof portion 428 and the vertical column 32, minimizing any pinch hazard. The base portion 426 and roof portion 428 also extend upwardly from the base 34 a sufficient distance such that a gap is defined between the interior upper surface of the roof portion 428 and the foot switch 420 to provide sufficient toe clearance for accessing the foot switch 420.

As can be appreciated, the foot switch roof 416 protects the foot switch 420 of the procedure table 24 without the hassle of using plastic bags or other cumbersome coverings.

Release Lever Assemblies

Referring to FIGS. 12 and 12A, the veterinary procedure table system 20 may further include one or more release lever assemblies that are easily operable by personnel during a procedure. More specifically, the veterinary procedure table system 20 may include one or more release lever assemblies for activating certain aspects of the procedure table 24, such as the tilt assembly 52 or the two panel V-top system.

Prior art systems typically include release lever assemblies that require visualization to operate. However, there is typically a drape covering the side of the procedure table, including the release lever assemblies. To avoid breaking the sterile field, the user has to put his or her hand under the drape and feel around for the lever, known as "drape diving".

The depicted veterinary procedure table system 20 includes release lever assemblies that minimize any drape diving. More specifically, the veterinary procedure table system 20 includes a first V-top lever assembly 434 located on a bottom surface of the first panel 64 and configured to operate the two panel V-top system 62 (see FIG. 11), a second V-top lever assembly 438 located on a bottom surface of the second panel 66 and configured to operate the two panel V-top system 62, and a tilt lever assembly 444 located beneath the first panel 64 and configured to operate the tilt-top mechanism. The first V-top lever assembly 434, second V-top lever assembly 438, and tilt lever assembly 444 are substantially identical, and therefore, only the second V-top lever assembly 438 will be described in detail.

The second V-top lever assembly 438 includes an L-shaped lever 446 that is pivotally coupled to a paddle mounting bracket 448. The paddle mounting bracket 448 includes a panel mounting portion 452 secured to the bottom surface of the second panel 66, and a cable mounting portion 454 extending substantially transversely from the panel-mounting portion 452 and configured to house or otherwise slidably receive a cable 456 connected to the lever 446.

The lever 446 includes a paddle portion 446 configured to be graspable by a user, and a cable-pulling portion 462 extending substantially transversely from the paddle portion 446 that connects to the end of the cable 456. The lever 446 is pivotally coupled to the panel-mounting portion 452 of the paddle mounting bracket 448 at a lever pivot 464 defined near the intersection of the paddle portion 446 and the cable-pulling portion 462. As such, when the paddle portion 446 is moved about the lever pivot 464, the cable-pulling portion 462 correspondingly moves to pull or release the cable 456. The paddle mounting bracket 448 may include a downwardly-turned edge extending from the panel mounting portion 452 that acts as a stop against the paddle portion 446 to limit the upward pivotal movement of the lever 446.

To enhance graspability of the lever 446, the paddle portion 446 may include an upwardly turned, widened end 466. The upwardly turned, widened end 466 is ergonomically designed to be graspable by a user without the need for visualization. Accordingly, the second V-top lever assembly 438 may be used without the need for drape diving.

Stabilizing Rail Accessory

Figure 14:
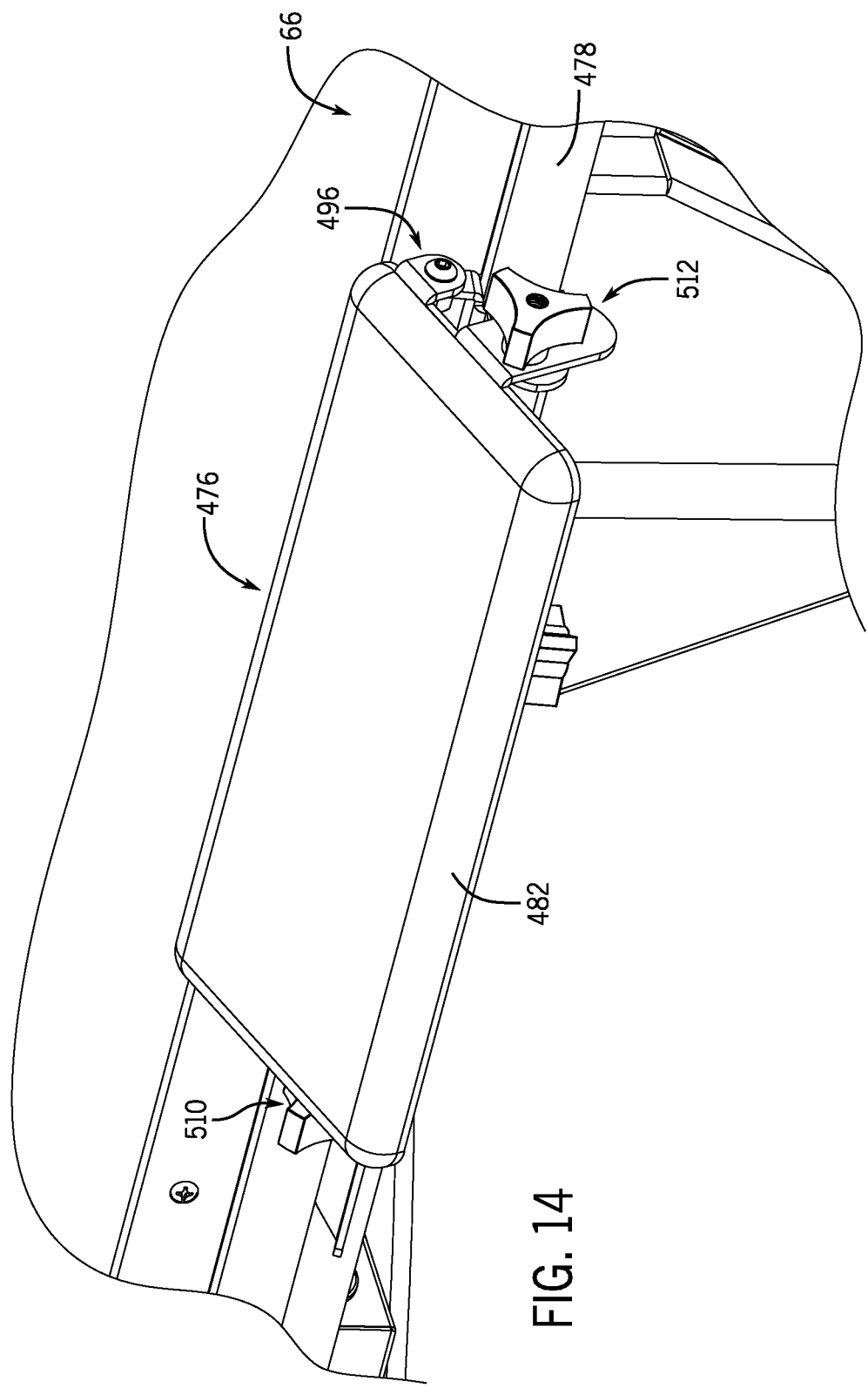
FIG. 14 shows an isometric zoomed-in view of the arm rest assembly of FIG. 13.
Figure 15:
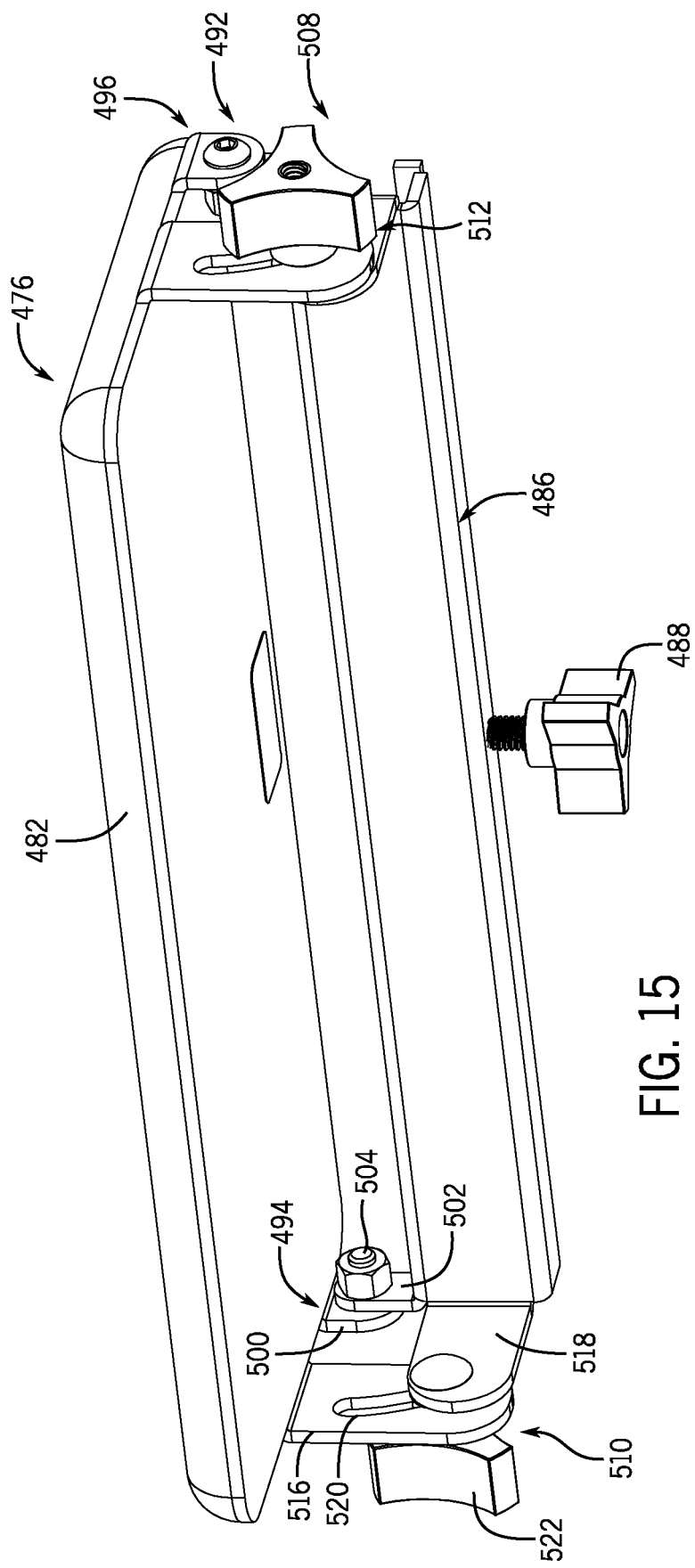
FIG. 15 shows an isometric view of the arm rest assembly of FIG. 14.

Referring to FIGS. 13-15, the veterinary procedure table system 20 may further include one or more rail accessories for providing stabilizing support to the practitioner or the animal during a procedure. For instance, the veterinary procedure table system 20 may include an armrest assembly 476 attachable to a rail 478 of the procedure table 24 that is configured to provide stabilizing support to a practitioner's arm, wrist, hand, etc., during delicate or precise procedures, such as eye surgery. The armrest assembly 476 includes a padded armrest 482 that is that is adjustable in orientation in an unlocked configuration and fixed in orientation in a locked configuration.

The padded armrest 482 is secured to a rail mount bracket 486, which is securable to a rail 478 extending along a side edge of the procedure table 24 at a location along the rail. The rail mount bracket 486 is generally U-shaped and configured to be slidably secured on the rail 478. A thumbscrew 488 passes transversely through the rail mount bracket 486 to engage the rail 478 and secure the rail mount bracket 486 against the rail 478.

The armrest 482 is movably secured to the rail mount bracket 486 such that the armrest 482 may be moved into a desired tilted orientation in the unlocked configuration. The armrest 482 is movably secured to the rail mount bracket 486 through an armrest pivot assembly 492. The armrest pivot assembly 492 includes a first pivot assembly 494 defined between first ends of the rail mount bracket 486 and the armrest 482 and a second pivot assembly 496 defined between second ends of the rail mount bracket 486 and the armrest 482. The first pivot assembly 494 is defined by a first flange 500 extending downwardly from a rear portion of the armrest 482 that overlaps with a second flange 502 extending upwardly from a top surface of the rail mount bracket 486. A pivot pin 504 passes through the first and second flanges 500 and 502 to allow the armrest 482 to pivot relative to the rail mount bracket 486 at its first end. The second pivot assembly 496 is substantially identical to the first pivot assembly 494 and therefore will not be separately described.

After the armrest 482 is moved about the pivot access of the first and second pivot assemblies 494 and 496 into a desired (e.g., tilted) orientation relative to the rail mount bracket 486, the armrest 482 is locked in its orientation to provide stabilizing support during the procedure. In that regard, the armrest assembly 476 further includes an armrest adjustment assembly 508 configured to lock the armrest 482 in its orientation.

The armrest adjustment assembly 508 includes a first thumbscrew assembly 510 defined between the first ends of the rail mount bracket 486 and the armrest 482 and a second thumb screw assembly 512 defined between the second ends of the rail mount bracket 486 and the armrest 482. The first and second thumb screw assemblies 510 and 512 selectively secure the first and second ends of the armrest 482 in the tilted orientation relative to the rail mount bracket 486.

The first thumb screw assembly 510 is defined by a third flange 516 extending downwardly from a middle portion of the armrest 482 that overlaps with a fourth flange 518 extending forwardly from a front side of the first end of the rail mount bracket 486. The third flange 516 includes an arced slot 520 that is alignable with an opening (not shown) in the fourth flange 518. A thumbscrew 522 passes through the arced slot 520 in the third flange 516 and through the opening in the fourth flange 518 and can be tightened in any position along the arced slot 520 to secure the armrest 482 in a desired (e.g., tilted) orientation. The second thumbscrew assembly 512 is substantially identical to the first thumb-screw assembly 510 and therefore will not be separately described.

To use the armrest assembly 476, the rail mount bracket 486 is secured to the rail 478 at a desired location along the length of the rail. If not already loosened, the thumbscrew 522 of the first and second thumb screw assemblies 510 and 512 is loosened such that the armrest 482 may pivot about the first and second pivot assemblies 494 and 496. The armrest 482 is moved about the first and second pivot assemblies 494 and 496 into a desired orientation. The thumbscrew 522 of the first and second thumb screw assemblies 510 and 512 may then be tightened to secure the armrest 482 in its orientation.

It should be appreciated that aspects of the armrest assembly 476 may be adapted for other uses, such as with limb holders, instruments holders, etc. As such, the term "armrest" should be broadly interpreted to cover any suitable use that would benefit from stabilization and/or support.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an exemplary embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C).

Language such as "raised", "lowered", "tilted", "non-tilted", "top", "bottom", "vertical", "horizontal", "lateral", etc., in the present disclosure is meant to provide orientation for the reader with reference to the drawings and is not intended to be the required orientation of the components or to impart orientation limitations into the claims.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, it may not be included or may be combined with other features.

As used herein, the terms "about" and "approximately," in reference to a number, is used herein to include numbers that fall within a range of 10%, 5%, or 1% in either direction (greater than or less than) the number unless otherwise stated or otherwise evident from the context (except where such number would exceed 100% of a possible value).

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A veterinary procedure table system comprising:
a procedure table having an animal support surface assembly supported by a vertical column, wherein the animal support surface assembly is movable between a first tilted orientation and a second tilted orientation, and wherein the vertical column is extendable along its longitudinal axis such that the animal support surface assembly is movable between a first animal support surface height position and a second animal support surface height position, wherein the animal support surface assembly comprises a first elongated panel, a second elongated panel, and a gap extending between the first and second elongated panels, wherein both of the first and second elongated panels extend across the procedure table from a first end of the procedure table and to a second end of the procedure table, wherein the first and second elongated panels are moveable between at least an elongated substantially flat, co-planar position and a V-shape position, and wherein the veterinary procedure table system further comprises:
a fluid collection and cleaning assembly configured to collect fluid flowing from the first and second elongated panels in an elongated channel located beneath the first and second elongated panels and further configured to enable cleaning of the elongated channel without having to remove the elongated channel from its location beneath the first and second elongated panels, wherein the elongated channel has a longitudinal axis and is disposed between a first lateral portion and a second lateral portion, and wherein the first and second elongated panels are spaced apart from the elongated channel, the first lateral portion, and the second lateral portion along the longitudinal axis of the elongated channel when the first and second elongated panels are in the V-shape position, wherein the fluid collection and cleaning assembly includes a first pivot plate coupled to the first and second elongated panels at the first end of the procedure table and a second pivot plate coupled to the first and second elongated panels at the second end of the procedure table, wherein the elongated channel extends between the first and second pivot plates such that a continuous opening is defined between the first and second elongated panels and the elongated channel, wherein the continuous opening extends the length of the procedure table from the first pivot plate to the second pivot plate, wherein the first and second pivot plates elevate the first and second elongated panels a sufficient distance above the elongated channel such that the continuous opening provides lateral access to an inside of the elongated channel between the first and second pivot plates without having to remove the elongated channel from its location beneath the first and second elongated panels; and a back table coupled to the vertical column of the procedure table through an articulating arm assembly, wherein the back table is movable between a first position relative to the procedure table and a second position relative to the procedure table, wherein the back table moves with the animal support surface assembly between the first animal support surface height position and the second animal support surface height position, wherein the back table does not tilt with the animal support surface assembly between the first tilted orientation and the second tilted orientation, wherein at least a portion of the articulating arm assembly is positioned beneath the procedure table, and wherein articulating arm assembly is configured to move the back table into at least first and second circumferential positions relative to the procedure table.

2. The veterinary procedure table system of claim 1, further comprising a linkage assembly located between the back table and the articulating arm assembly configured to move the back table relative to the procedure table between a first back table height position and a second back table height position.

3. The veterinary procedure table system of claim 2, wherein the linkage assembly includes a first link located at a first end of the linkage assembly, a second link located at a second end of the linkage assembly opposite the first end, a third link extending between the first and second links, and a fourth link extending between the first and second links.

4. The veterinary procedure table system of claim 3, wherein the first link is pivotally coupled to the third link through a first pivot assembly, the third link is pivotally coupled to the second link through a second pivot assembly, the first link is pivotally coupled to the fourth link through a third pivot assembly, and the fourth link is pivotally coupled to the second link through a fourth pivot assembly, and wherein the first, second, third, and fourth links are in a first parallelogram arrangement when the linkage assembly is in a lowered position and the first, second, third, and fourth links are in a second parallelogram arrangement when the linkage assembly is in a raised position.

5. The veterinary procedure table system of claim 4, wherein a distance between the first link is pivotally coupled to the third link through a first pivot assembly, the third link is pivotally coupled to the second link through a second pivot assembly, the first link is pivotally coupled to the fourth link through a third pivot assembly, and the fourth link is pivotally coupled to the second link through a fourth pivot assembly, and wherein the first, second, third, and fourth links are in a first parallelogram arrangement when the linkage assembly is in a lowered position and the first, second, third, and fourth links are in a mirrored, second parallelogram arrangement when the linkage assembly is in a raised position.

6. The veterinary procedure table system of claim 5, wherein a shift of the first, second, third, and fourth pivot assemblies from the first parallelogram arrangement into the mirrored, second parallelogram arrangement moves the second link along an arced upward path until the linkage assembly reaches the raised position.

7. The veterinary procedure table system of claim 6, wherein as the arrangement of the first, second, third, and fourth pivot assemblies shift from the first parallelogram arrangement into the mirrored, second parallelogram arrangement, the distance between the first and second pivot assemblies remains fixed, the distance between the third and fourth pivot assemblies remains fixed, the distance between the first and third pivot assemblies remains fixed, and the distance between the second and fourth pivot assemblies remains fixed such that the second link remains in a substantially horizontal orientation as it travels along the arced upward path toward the raised position.

8. The veterinary procedure table system of claim 4, wherein as the linkage assembly is moved between lowered and raised positions, the first, second, and fourth links move into and out of at least a partially nested configuration within the third link.

9. The veterinary procedure table system of claim 1, wherein the back table moves with the vertical column when the vertical column extends to move the animal support surface assembly from the first animal support surface height position to the second animal support surface height position.

10. The veterinary procedure table system of claim 1, wherein the first elongated panel includes a first elongated panel support secured to an underside of the first elongated panel that extends between an outer elongated edge of the first elongated panel toward an inner elongated edge of the first elongated panel, wherein the first elongated panel support includes a first inner elongated edge that is at least one of contoured or recessed to increase the distance between the underside of the first elongated panel and the elongated channel.

11. The veterinary procedure table system of claim 1, wherein a first angled portion couples the first lateral portion to a first end of the elongated channel, and a second angled portion couples the second lateral portion to a second end of the elongated channel.

12. The veterinary procedure table system of claim 1, wherein the fluid collection and cleaning assembly includes a fluid flow directing assembly configured to help direct the flow of fluid into the elongated channel, the fluid flow directing assembly defined by an overlap of a downwardly-turned front face of the first elongated panel and a downwardly-turned elongated side face of the first elongated panel.

13. The veterinary procedure table system of claim 1, further comprising a foot switch assembly having a foot switch secured to a base and a foot switch roof configured to at least partially cover the foot switch.

14. The veterinary procedure table system of claim 1, further comprising at least one release lever assembly configured to operate aspects of the procedure table, the at least one release lever assembly including an L-shaped lever pivotally coupled to a mounting bracket, the mounting bracket secured beneath the animal support surface assembly.

15. The veterinary procedure table system of claim 1, further comprising an arm rest assembly attachable to a rail of the procedure table that is adjustable in orientation in an unlocked configuration and fixed in orientation in a locked configuration.

16. A veterinary procedure table system comprising:
a procedure table having an animal support surface assembly supported by a vertical column, wherein the animal support surface assembly comprises:
a first elongated panel;
a second elongated panel;
a gap extending between the first and second elongated panels, wherein the first and second elongated panels are moveable between at least an elongated substantially flat, co-planar position and a V-shape position; and a fluid collection and cleaning assembly configured to collect fluid flowing from the first and second elongated panels in an elongated channel located beneath the first and second elongated panels and further configured to enable cleaning of the elongated channel without having to remove the elongated channel from its location beneath the first and second elongated panels, wherein the elongated channel has a longitudinal axis and is disposed between a first lateral portion and a second lateral portion, wherein the first and second elongated panels are spaced apart from the first lateral portion, the second lateral portion, and the elongated channel along the length of the longitudinal axis when the first and second elongated panels are in the V-shape position, wherein both of the first and second elongated panels extend across the procedure table from a first end of the procedure table and to a second end of the procedure table, wherein the fluid collection and cleaning assembly includes first and second pivot plates that elevate the first and second elongated panels a sufficient distance above the elongated channel such that a user may access the elongated channel for cleaning without having to remove the elongated channel from its location beneath the first and second elongated panels, wherein the first pivot plate is coupled to both the first and second elongated panels at the first end of the procedure table, wherein the second pivot plate is coupled to both the first and second elongated panels at the second end of the procedure table, wherein the elongated channel extends between the first and second pivot plates such that a continuous opening is defined between the bottom of first and second elongated panels and the elongated channel, wherein the continuous opening extends the length of the procedure table from the first pivot plate to the second pivot plate and provides lateral access to an inside of the elongated channel between the first and second pivot plates such that the user may laterally access the elongated channel between the first and second pivot plates.

* * * * *

UNITED STATES PATENT AND TRADEMARK OFFICE
CERTIFICATE OF CORRECTION

| | | |
|---|---|---|
| PATENT NO. | : 12,285,315 B2 | Page 1 of 1 |
| APPLICATION NO. | : 17/182688 | |
| DATED | : April 29, 2025 | |
| INVENTOR(S) | : Joseph D. Reback and Cole Jason Dalton | |

It is certified that error appears in the above-identified patent and that said Letters Patent is hereby corrected as shown below:

In the Claims

In Claim 1, Column 21, Line 17, insert --the-- between "and wherein" and "articulating arm".

Signed and Sealed this
Sixteenth Day of September, 2025

Coke Morgan Stewart
*Acting Director of the United States Patent and Trademark Office*